United States Patent
Sirhan et al.

(10) Patent No.: US 7,238,168 B2
(45) Date of Patent: Jul. 3, 2007

(54) EXCHANGEABLE CATHETER

(75) Inventors: Motasim Sirhan, Sunnyvale, CA (US); John Yan, Los Gatos, CA (US); Kevin Gertner, Los Gatos, CA (US)

(73) Assignee: Avantec Vascular Corporation, Sunnyvale, CA (US)

( * ) Notice: Subject to any disclaimer, the term of this patent is extended or adjusted under 35 U.S.C. 154(b) by 261 days.

(21) Appl. No.: 10/080,920

(22) Filed: Feb. 20, 2002

(65) Prior Publication Data

US 2002/0133217 A1    Sep. 19, 2002

Related U.S. Application Data

(63) Continuation-in-part of application No. 10/001,210, filed on Nov. 30, 2001, now abandoned, which is a continuation-in-part of application No. 09/872,640, filed on May 31, 2001, now Pat. No. 7,131,986, which is a continuation-in-part of application No. 09/585,943, filed on Jun. 2, 2000, now Pat. No. 6,569,180.

(51) Int. Cl.
*A61M 29/00* (2006.01)
*A61B 25/00* (2006.01)

(52) U.S. Cl. .............. 604/96.01; 604/528; 604/523; 604/264; 606/194; 623/1.11

(58) Field of Classification Search .............. None
See application file for complete search history.

(56) References Cited

U.S. PATENT DOCUMENTS

| | | | |
|---|---|---|---|
| 4,655,746 A | 4/1987 | Daniels et al. | |
| 4,748,982 A | 6/1988 | Horzewski et al. | |
| 4,762,129 A * | 8/1988 | Bonzel | ........................ 606/194 |
| 4,947,864 A | 8/1990 | Shockey et al. | |
| 4,988,356 A | 1/1991 | Crittenden et al. | |
| 5,040,548 A | 8/1991 | Yock | |
| 5,061,273 A | 10/1991 | Yock | |
| 5,135,535 A * | 8/1992 | Kramer | ........................ 606/194 |
| 5,195,978 A | 3/1993 | Schiffer | |
| 5,232,445 A | 8/1993 | Bonzel | |
| 5,263,963 A | 11/1993 | Garrison et al. | |
| 5,281,203 A | 1/1994 | Ressemann | |
| 5,300,085 A | 4/1994 | Yock | |
| 5,328,472 A | 7/1994 | Steinke et al. | |
| 5,334,147 A | 8/1994 | Johnson | |
| 5,336,184 A | 8/1994 | Teirstein | |
| 5,346,505 A | 9/1994 | Leopold | |
| 5,350,395 A | 9/1994 | Yock | |
| 5,364,376 A | 11/1994 | Horzewski et al. | |
| 5,380,283 A | 1/1995 | Johnson | |
| 5,383,853 A | 1/1995 | Jung et al. | |
| 5,395,335 A * | 3/1995 | Jang | ........................ 606/194 |
| 5,413,559 A | 5/1995 | Sirhan et al. | |
| 5,451,233 A | 9/1995 | Yock | |

(Continued)

FOREIGN PATENT DOCUMENTS

| | | |
|---|---|---|
| WO | WO 97/07756 | 3/1997 |
| WO | WO 99/13935 | 2/1999 |

*Primary Examiner*—Glenn K. Dawson
(74) *Attorney, Agent, or Firm*—Townsend and Townsend and Crew LLP

(57) ABSTRACT

An intravascular balloon catheter includes a tubular catheter body having a balloon structure removably mounted over the catheter body. The catheter body has a guidewire lumen, and the catheter body may be left in place within a patient's vasculature while the balloon structure is withdrawn and optionally a second balloon structure introduced over the catheter body. The catheter and methods of the present invention are particularly suitable for performing angioplasty and subsequent procedures, such as stent placement, which are best performed using successive interventional balloon structures.

35 Claims, 18 Drawing Sheets

U.S. PATENT DOCUMENTS

| | | |
|---|---|---|
| 5,458,613 A | 10/1995 | Gharibadeh et al. |
| 5,460,185 A | 10/1995 | Johnson et al. |
| 5,462,529 A | 10/1995 | Simpson et al. |
| 5,468,225 A | 11/1995 | Teirstein |
| 5,472,425 A | 12/1995 | Teirstein |
| 5,501,227 A | 3/1996 | Yock |
| 5,531,690 A | 7/1996 | Solar |
| 5,533,968 A | 7/1996 | Muni et al. |
| 5,545,134 A | 8/1996 | Hilaire et al. |
| 5,554,118 A | 9/1996 | Jang |
| 5,571,094 A | 11/1996 | Sirhan |
| 5,578,009 A * | 11/1996 | Kraus et al. ............... 606/192 |
| 5,607,406 A | 3/1997 | Hernandez et al. |
| 5,613,946 A * | 3/1997 | McKeever ............... 606/194 |
| 5,620,417 A | 4/1997 | Jang et al. |
| 5,626,600 A | 5/1997 | Horzewski et al. |
| 5,685,312 A | 11/1997 | Yock |
| 5,709,658 A | 1/1998 | Sirhan et al. |
| 5,728,067 A | 3/1998 | Enger |
| 5,738,667 A | 4/1998 | Solar |
| 5,749,888 A | 5/1998 | Yock |
| 5,755,685 A | 5/1998 | Andersen |
| 5,769,868 A | 6/1998 | Yock |
| 5,776,141 A | 7/1998 | Klein et al. |
| 5,807,355 A | 9/1998 | Ramzipoor et al. |
| 5,810,869 A | 9/1998 | Kaplan et al. |
| 5,814,061 A | 9/1998 | Osborne et al. |
| 5,820,595 A | 10/1998 | Parodi |
| 5,827,241 A | 10/1998 | Douk et al. |
| 5,830,227 A | 11/1998 | Fischell et al. |
| 5,833,659 A | 11/1998 | Kranys |
| 5,836,987 A | 11/1998 | Schneider et al. |
| 5,846,246 A | 12/1998 | Dirks et al. |
| RE36,104 E * | 2/1999 | Solar ............... 606/194 |
| 5,865,801 A | 2/1999 | Houser |
| 5,891,056 A | 4/1999 | Ramzipoor |
| 5,910,154 A | 6/1999 | Tsugita et al. |
| 5,919,164 A | 7/1999 | Andersen |
| 5,919,175 A | 7/1999 | Sirhan |
| 5,921,971 A | 7/1999 | Agro et al. |
| 5,944,691 A | 8/1999 | Querns et al. |
| 5,947,927 A | 9/1999 | Mertens |
| 5,980,486 A | 11/1999 | Enger |
| 5,989,281 A | 11/1999 | Barbut et al. |
| 6,007,517 A | 12/1999 | Anderson |
| 6,044,845 A | 4/2000 | Lewis |
| 6,048,484 A | 4/2000 | House et al. |
| 6,056,722 A | 5/2000 | Jayaraman |
| 6,156,005 A | 12/2000 | Théron |
| 6,168,579 B1 | 1/2001 | Tsugita |
| 6,196,995 B1 | 3/2001 | Fagan |
| 6,200,305 B1 | 3/2001 | Berthiaume et al. |
| 6,264,671 B1 | 7/2001 | Stack et al. |
| 6,299,595 B1 | 10/2001 | Dutta et al. |
| 6,379,345 B1 | 4/2002 | Constantz |
| 6,398,792 B1 | 6/2002 | O'Connor |
| 6,416,529 B1 | 7/2002 | Holman et al. |
| 6,569,180 B1 * | 5/2003 | Sirhan et al. ............... 606/194 |
| 7,131,986 B2 * | 11/2006 | Sirhan et al. ............... 606/194 |

* cited by examiner

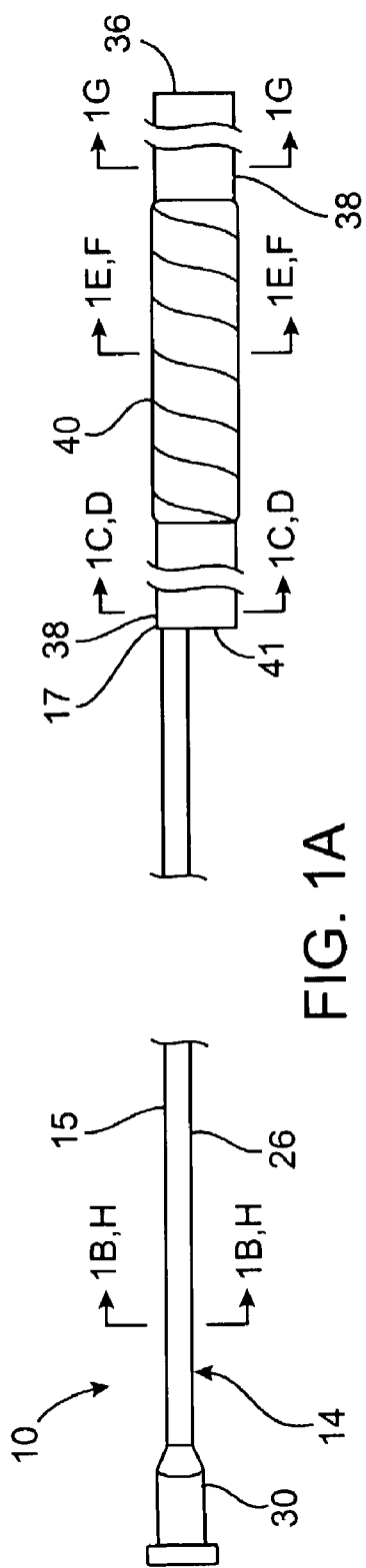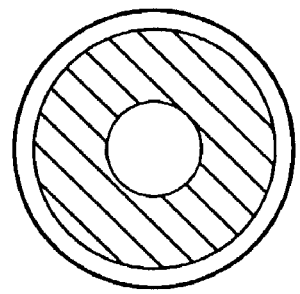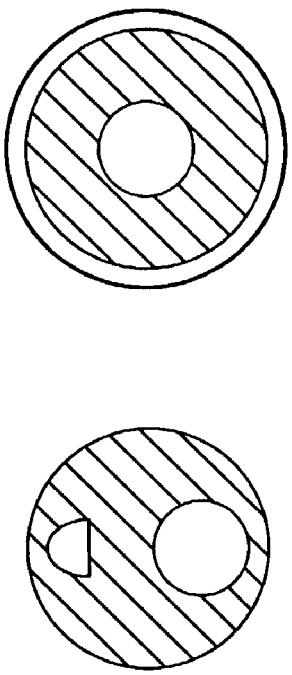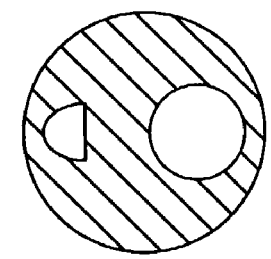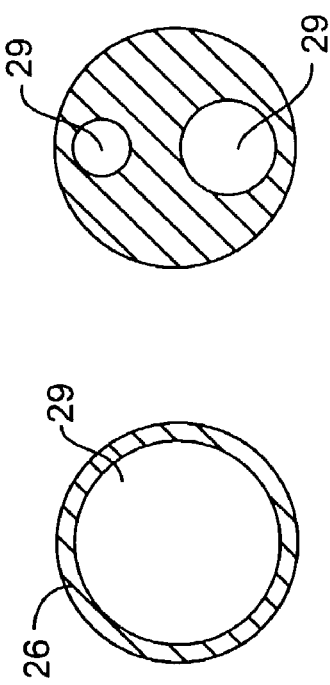

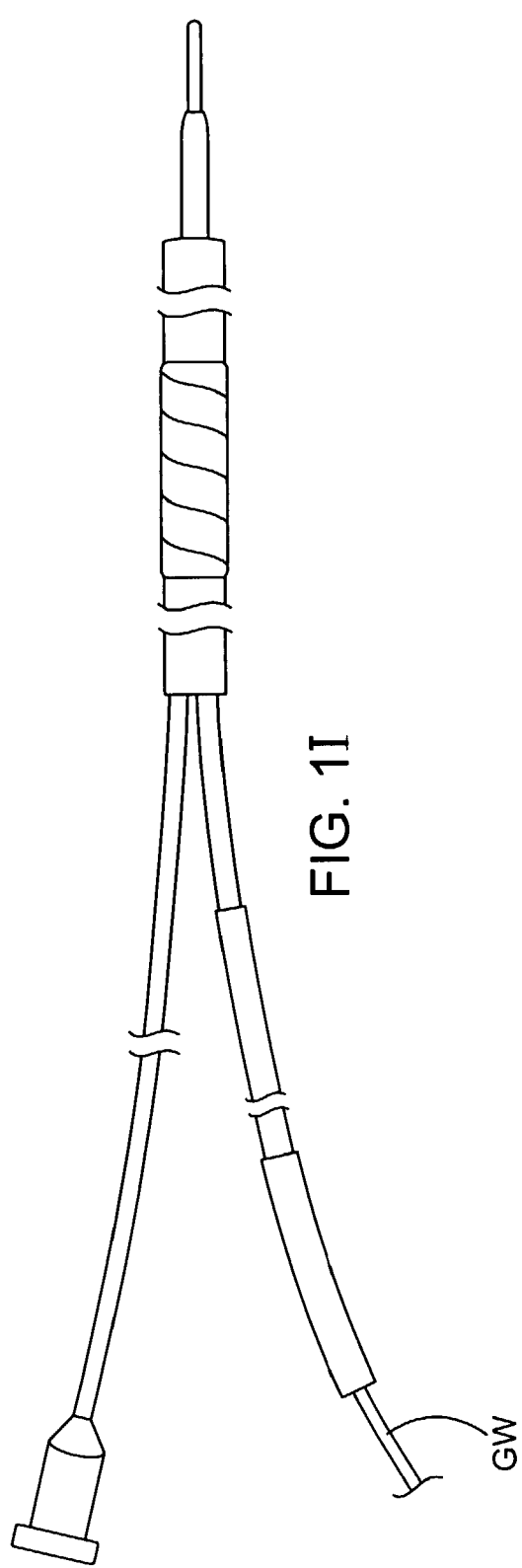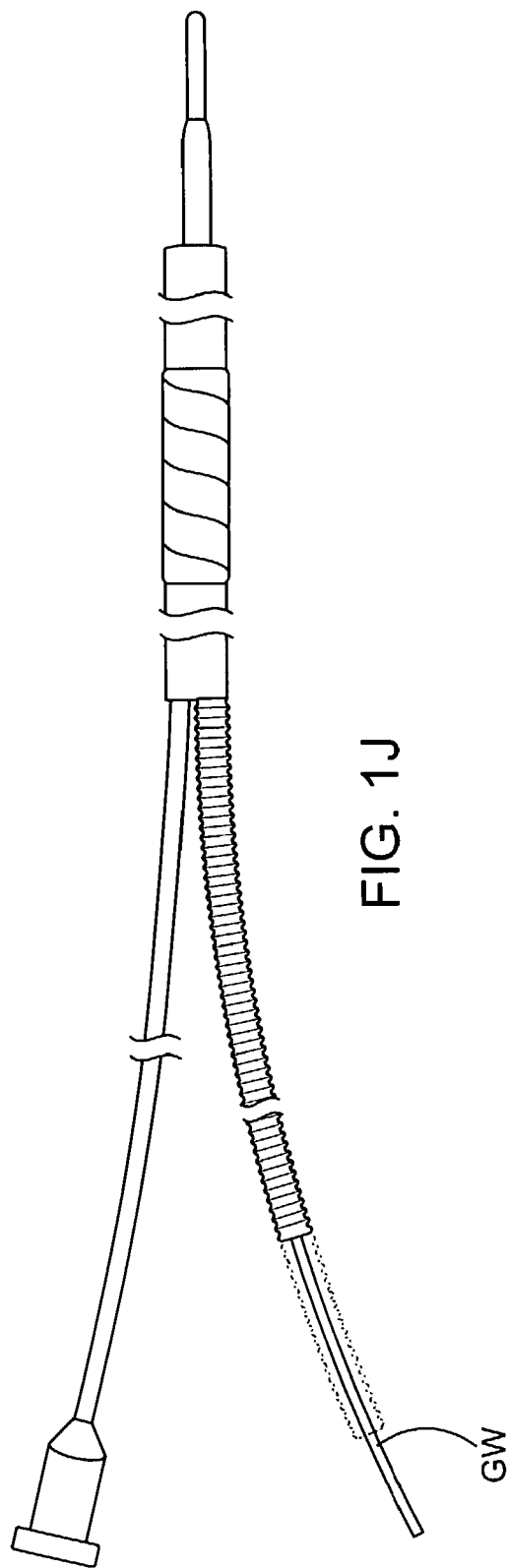

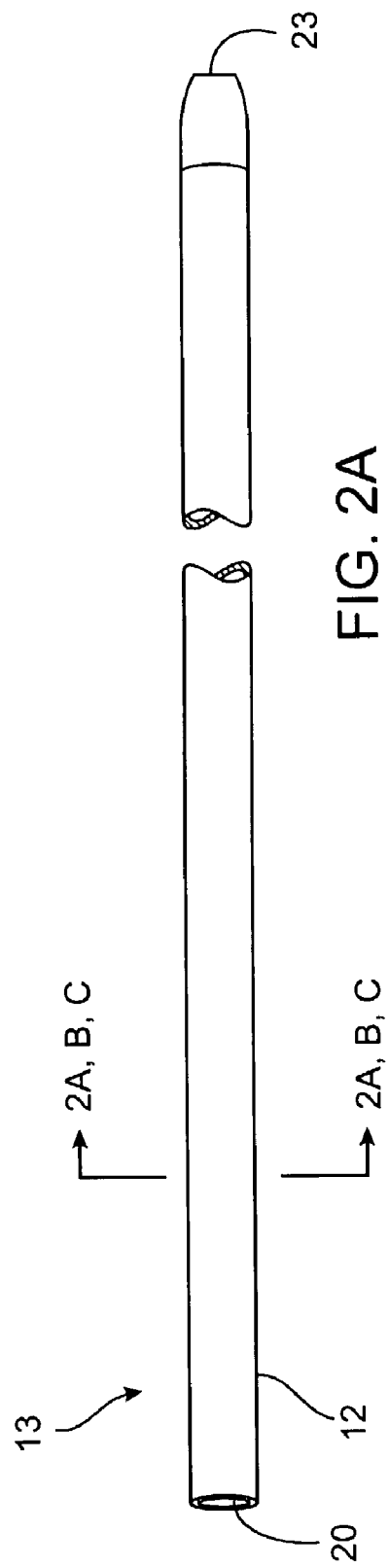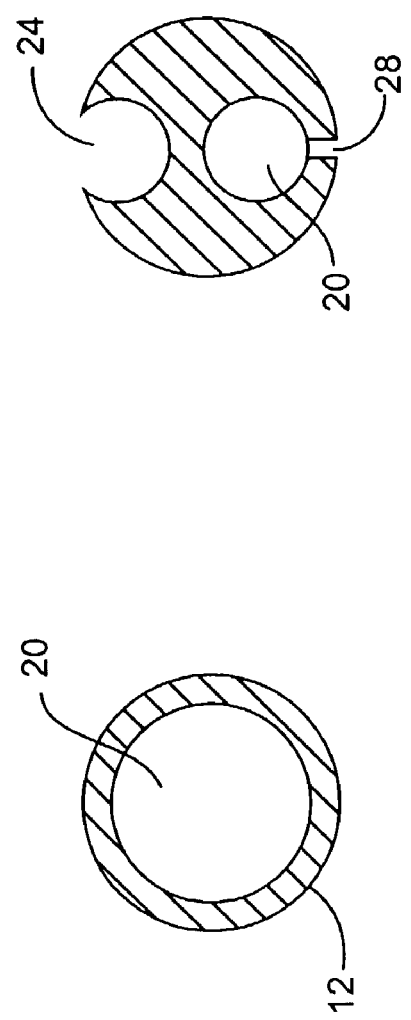

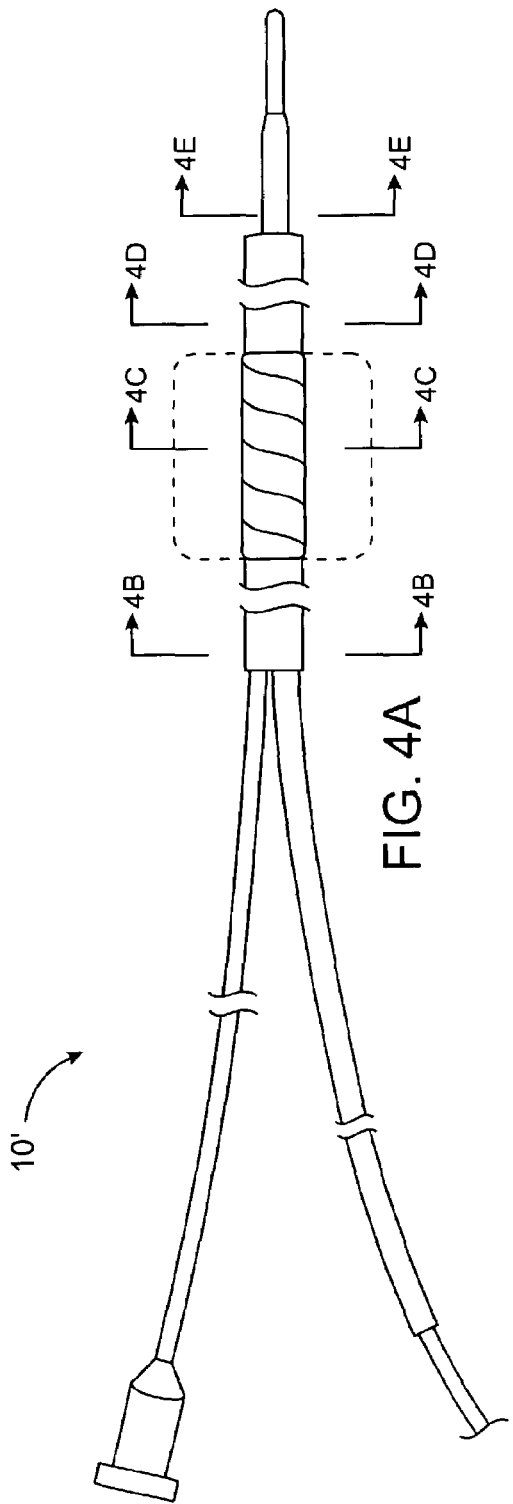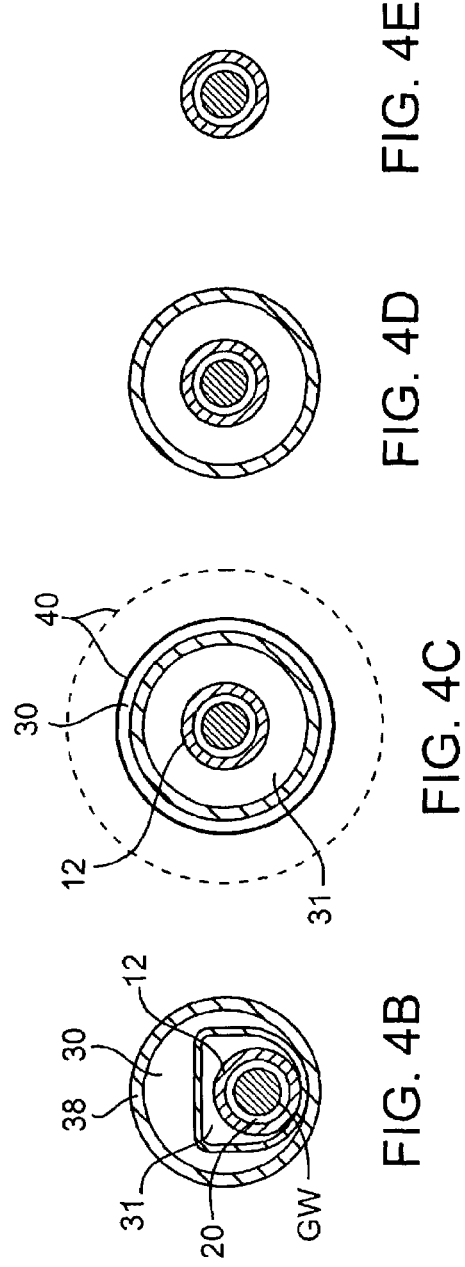

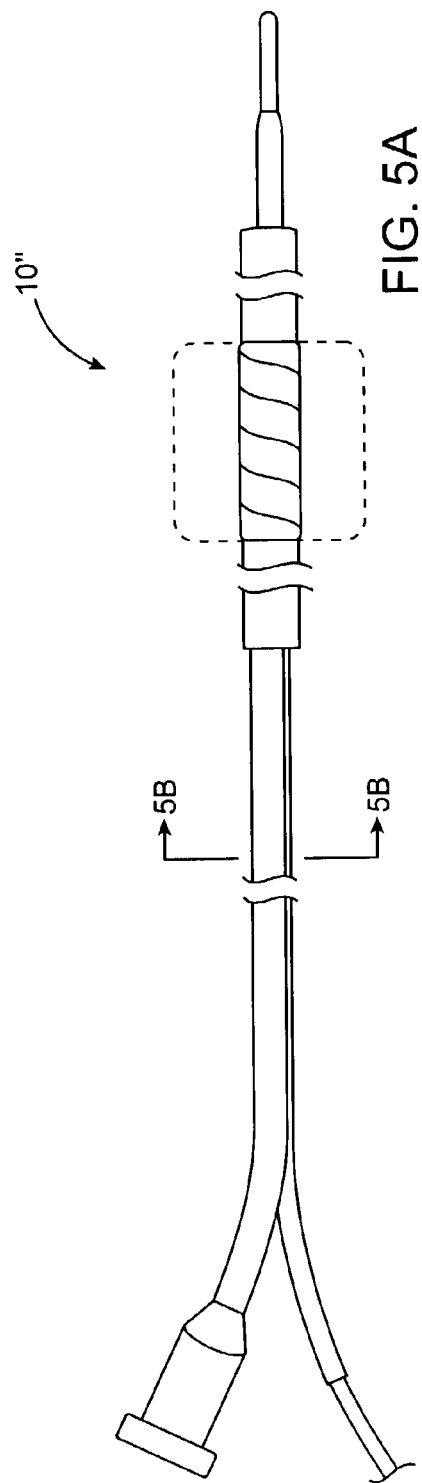
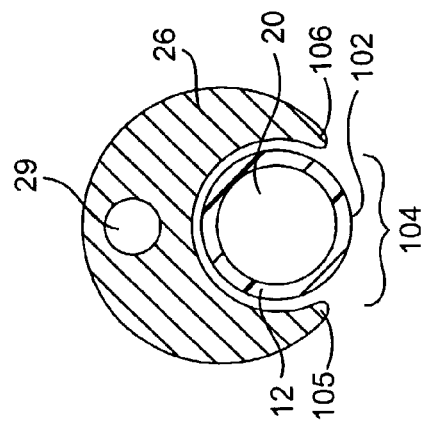
FIG. 5A
FIG. 5B

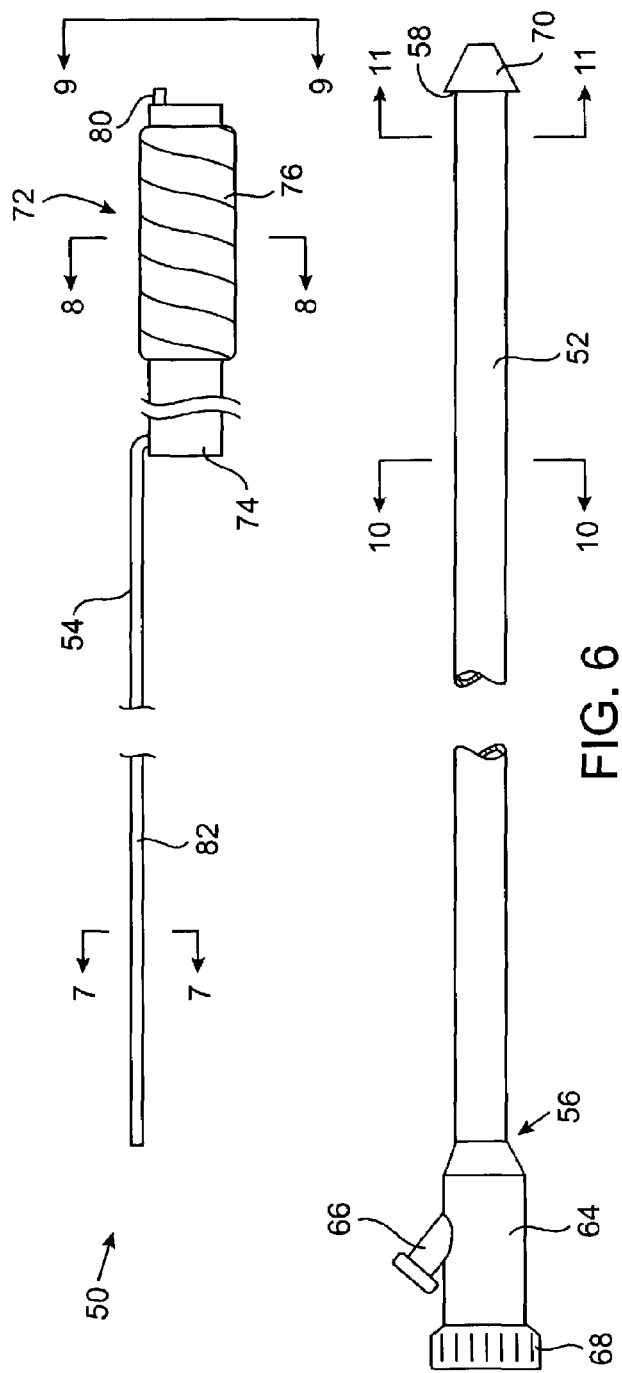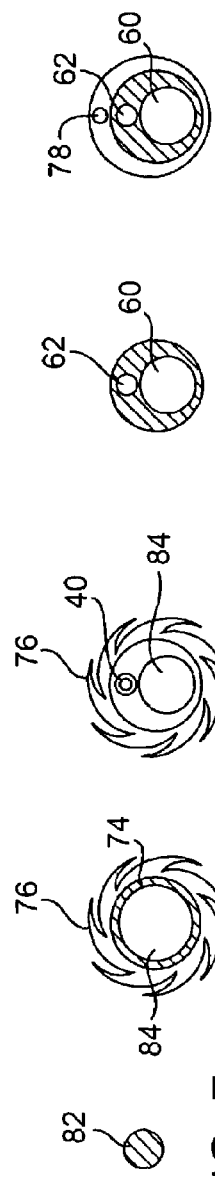
FIG. 6  FIG. 7  FIG. 8  FIG. 9  FIG. 10  FIG. 11

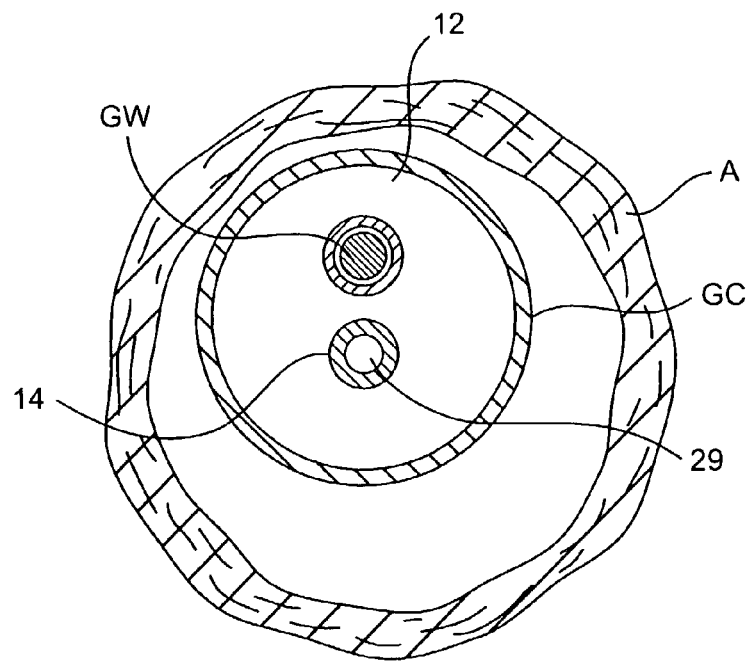
FIG. 13
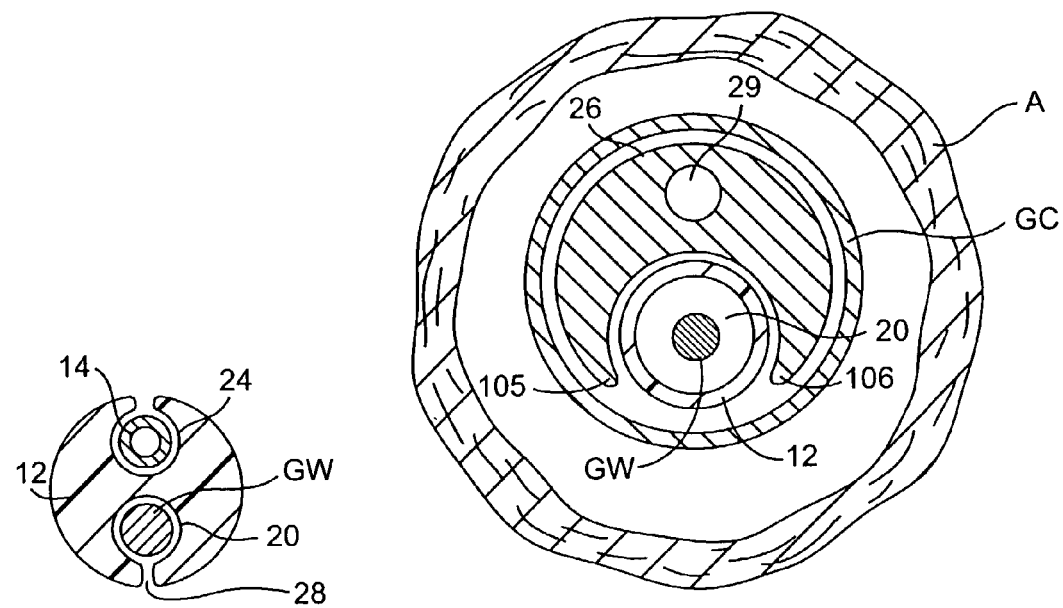
FIG. 13A
FIG. 13'

EXCHANGEABLE CATHETER

CROSS-REFERENCES TO RELATED APPLICATIONS

The present application is a continuation-in-part and claims the benefit of priority from U.S. patent application Ser. No. 10/001,210 filed Nov. 30, 2001, now abandoned which was a continuation-in-part of U.S. patent application Ser. No. 09/872,640 filed May 31, 2001, now U.S. Pat. No. 7,131,986 which was a continuation-in-part of U.S. patent application Ser. No. 09/585,943 filed Jun. 2, 2000, now U.S. Pat. No. 6,569,180 the full disclosures of which are incorporated herein by reference.

BACKGROUND OF THE INVENTION

The present invention relates generally to medical devices and methods. More particularly, the present invention relates to a balloon catheter having an exchangeable balloon structure.

Percutaneous transluminal angioplasty procedures have become a therapy of choice for treating stenosed regions in the patient's vasculature, particularly the coronary vasculature. Recently, the use of such angioplasty procedures has often been combined with stent placement and/or radiation treatment to inhibit restenosis and hyperplasia following angioplasty. When performing such multiple, sequential treatments, it is usually necessary to "exchange" catheters which are used to perform each of the procedures. That is, the initial angioplasty treatment will be performed using a balloon angioplasty catheter. After the angioplasty is completed, a second catheter carrying a stent or other vascular prosthesis must then be introduced to the treatment site. Introduction of the second catheter involves first removing the balloon angioplasty catheter and then placing the second catheter in the treatment region. Optionally, a third catheter may then be exchanged for the second in order to perform radiation or other treatments in order to inhibit hyperplasia.

In performing such multiple, sequential treatments, most physicians prefer to leave a "guidewire" in place to the treatment location. A guidewire is a small diameter, highly flexible wire that can be steered to the target location through the vasculature and which then acts as a guide path for introducing and positioning the balloon angioplasty and other interventional catheters.

In the early days, balloon angioplasty catheters were designed to be introduced into the vasculature in an "over-the-wire" manner. That is, the catheters were designed to have passages, commonly referred to as guidewire lumens, which extended the entire distance from the distal end of the catheter to the proximal end of the catheter. The catheter could then be loaded over a proximal end of a guidewire which was already in place in the patient and then advanced over the guidewire until a distal end of the catheter reached the target site. While functional, the need to maintain control of the guidewire while the interventional catheter was being introduced meant that the guidewire had to have an excess length outside of the patient which was greater than the length of the catheter being introduced. If the length were any shorter, the treating physician would not be able to hold on to the guidewire as the catheter was being introduced. Although necessary for catheter introduction, the excess guidewire length (optionally in the form of a detachable extension) was very difficult to manage during other parts of the treatment.

To overcome the difficulties associated with very long guidewires "rapid exchange" or "monorail" balloon angioplasty catheters were developed. A number of specific designs have been developed over the years, and the rapid exchange catheters generally have a shortened guidewire lumen which extends from a distal tip of the catheter to an exit port located closer to the distal end of the catheter than to the proximal end. By reducing the length of the guidewire lumen, the need for a guidewire having excess length outside of the patient is also reduced.

The use of rapid exchange catheters has become wide spread, and they have proven to be particularly valuable for use as stent delivery catheters. Stent delivery catheters are normally used after an initial angioplasty treatment. In such cases, the angioplasty catheter will be removed and exchanged for the stent delivery catheter. Use of an angioplasty catheter having a rapid exchange design facilitates removal of the angioplasty catheter over short guidewires. Similarly, use of the stent delivery catheter having a rapid exchange design facilitates introduction of the catheter over the guidewire which remains in place in the patient.

Despite their widespread acceptance, rapid exchange catheters suffer from a number of limitations. In particular, the shortened guidewire lumens reduce the "pushability" of the rapid exchange catheters. The use of full length guidewire lumens as provided by the over-the-wire designs results in an overall increase in the column strength of the catheter being introduced. That is, the catheter derives column strength not only from the catheter body itself, but also from the guidewire which is in place in the guidewire lumen over the entire length of the catheter, allowing better access across tight lesions. Additionally, presence of the guidewire in a full length guidewire lumen lessens the risk of the catheter body kinking or collapsing in tortuous regions of the vasculature. Kinking can be a particular problem at the point where the guidewire exits a catheter body in a rapid exchange design.

The second problem associated with the use of rapid exchange catheters is the inability to exchange the guidewire. Guidewire exchange in over-the-wire catheters is quite simple since the guidewire lumen extends the full length of the catheter body. In rapid exchange catheters, in contrast, there is no guidewire lumen in the proximal portions of the angioplasty catheter. It is therefore difficult to reintroduce a guidewire into the shortened guidewire lumen of the rapid exchange catheter.

For these reasons, it would be desirable to provide improved apparatus, methods, and kits which permit the exchange of catheters and catheter components over shortened guidewires. Particularly, it would be desirable to provide improved balloon angioplasty and other catheters which can be introduced to the vasculature in the manner of an over-the-wire catheter, but which allow removal of the catheter over a shortened guidewire and/or which permits exchange of catheter components over the catheter body which remains in place over the guidewire. It would be further desirable to provide balloon catheters and methods for their use which permit exchange of balloon structures over the catheter body while the catheter body remains in place in the vasculature over a guidewire and where the replacement balloon structure may optionally carry a stent. At least some of these objectives will be met by the invention described in claims herein after.

Accordingly, it would be a significant advance to provide improved devices and methods for reducing, inhibiting, or treating restenosis and hyperplasia which may follow angioplasty and other interventional treatments. This invention satisfies at least some of these and other needs.

BRIEF SUMMARY OF THE INVENTION

The present invention is directed to an intracorporeal devices and methods using the same, and more particularly, to intraluminal devices such as catheters including balloon catheters. The devices of the present invention may be used for performing diagnostic and/or treatment applications. The present devices are suitable for use for the treatment of a variety of conditions within different locations of a patient's corporeal body including the patient's vasculature. In particular, the devices can be used in the coronary, peripheral, and cerebral regions of a patient's vasculature for virtually any treatment modality that relies on balloon expansion, particularly angioplasty, stent placement, and the like.

As used herein, the term "intracorporeal body" refers to a body lumens or internal corporeal tissues and organs, within a corporeal body. The body lumen may be any blood vessel in the patient's vasculature, including veins, arteries, aorta, and particularly including coronary and peripheral arteries, as well as previously implanted grafts, shunts, fistulas, and the like. It will be appreciated that the present invention may also be applied to other body lumens, such as the biliary duct, which are subject to excessive neoplastic cell growth. Examples of internal corporeal tissues and organs, include various organs, nerves, glands, ducts, and the like.

In one embodiment, the intravascular catheters of the present invention comprise a treatment or diagnostic structure. In one embodiment the treatment or diagnostic structure is a balloon structure. Without any limitations intended, a balloon structure will be used to further describe the different features and embodiments of the present invention. The balloon structure includes a passage which is slidably receivable over other elongate bodies. The passage enables the selective introduction and/or removal of the treatment or diagnostic structure over the other catheter body facilitating the exchange of the balloon structure with another structure (e.g., another balloon structure or a non-balloon structure) at any time, before, during, or after the performance of treatment or diagnosis, in particular an intravascular interventional procedure employing the balloon structure.

In an embodiment, the device of the invention is an intravascular catheter comprising a balloon structure including an elongate shaft having a proximal end, a distal end, and proximal and distal sections. At least one lumen such as an inflation lumen extends along at least a portion of the shaft terminating at a point proximal to the distal end of the shaft. The shaft may be of a unitary construction or formed from more than one fluidically connected portions.

In an embodiment, an expandable member, such as an inflatable member (e.g., balloon) having an interior chamber is disposed at the distal section of the elongate shaft. The chamber, such as an inflation chamber, is in fluid communication with the inflation lumen.

The shaft further includes a sleeve portion at the shaft distal section, having an axial passage therethrough which is configured to be slidably disposed over the elongate body. For example, the passage is configured to be receivable over the elongate body or slidably receive the elongate body. At least a portion of the sleeve forms the inflation lumen extending within the inflatable member.

The sleeve may be formed as an integral part of the shaft. Alternatively, the sleeve portion may be formed from a separate element sealingly attached to a tubular member forming a portion of the shaft extending proximal to the sleeve.

In an embodiment, the sleeve portion includes multiple lumens, with at least one lumen being an inflation lumen and at least another lumen forming the passage for receiving the catheter body. The multiple lumens of the sleeve portion may be of a unitary construction or from different tubular members having lumens extending therein.

The balloon is disposed over at least a portion of the sleeve and is sealingly secured at balloon proximal and distal ends to the sleeve. Alternatively, the balloon may be formed integral with the sleeve. Usually, the sleeve portion has a longitudinal dimension greater than that of the balloon and extends distal to the balloon distal end.

The sleeve may have a length in the range from about 3 cm to about 50 cm, usually from about 4 cm to about 40 cm, and typically from about 5 cm to about 25 cm. The balloon or other expandable structure will generally have a length less than that of the sleeve, usually much shorter, typically being in the range from about 1 cm to about 5 cm, often from about 2 cm to about 4 cm. The sleeve may be formed from conventional catheter materials, typically being an extruded polymer tube.

In an embodiment, the balloon structure includes an axial groove extending along at least a portion of the shaft so as to removably receive at least a portion of the elongate body such as a catheter or a guidewire. The catheter structure axial groove may comprise a single groove or multiple intermittent grooves.

The balloon structure groove is appropriately sized to accommodate elongate bodies such as conventional guidewires and catheters, as well as catheter bodies disclosed herein. The balloon structure groove will usually have an inner diameter ranging from about 0.0145 inches to 0.03 inches, preferably from about 0.016 inches to 0.02 inches. The groove will typically have includes transverse ends. The groove transverse ends may overlap, abut, or have an opening formed therebetween. The opening between the transverse ends may range from about 00.1 inches to about 0.1 inches, and usually from about 0.001 inches to about 0.014 inches. The groove may generally have a length in the range from about 1 centimeters (cm) to about 200 cm, usually from about 1 cm to about 150 cm, and typically from about 10 cm to about 150 cm.

In embodiments including the axial groove, the elongate body (e.g., guidewire) may be disposed, at least partially, within the groove during the procedure. The positioning of the elongate body such as the guidewire within the groove will provide push strength necessary for improved advancement of the elongate body within the corporeal body. This will also help reduce buckling of at the shaft.

In another embodiment, the device of the invention further includes an intravascular catheter comprising a catheter body including an elongate member having proximal and distal ends and a guidewire receiving lumen extending along at least a portion therebetween to a port at the distal end of the elongate member. In an embodiment, the guidewire receiving lumen extends the entire length of the catheter body extending from a proximal port at the proximal end to the distal port. The catheter body may include one or more lumens. The catheter body may be of unitary construction or may be formed from different members fluidically connected to one another. The guidewire receiving lumen may be an integral part of the catheter body or may be formed as a lumen within another tubular body disposed within the catheter body. In one embodiment, the catheter body includes a split, fluidically connecting the exterior surface of the catheter body to the guidewire receiving lumen to facilitate insertion or removal of the guidewire, within or from the guidewire receiving lumen. In another embodiment, the catheter body may include a breakaway feature which allows opening the guidewire lumen to facilitate guidewire removal. The perimeter of the catheter body may have any suitable shape including circular, oblong, or elliptical shape.

The distal end of the catheter body, preferably, is axially tapered for improved navigation through the tortuous path of the intracorporeal body, usually for a length of at least 3 millimeters (mm), typically at least about 0.5 mm, preferably at least about 0.1 mm. The catheter body, may further include an atraumatic distal tip.

In an embodiment, the catheter body includes an axial groove extending along at least a portion of its length for slidably receiving at least a portion of another body, such as another catheter body, for example, the balloon structure. The catheter body groove is appropriately sized to accommodate balloon structures as disclosed herein or any other intravascular catheter as known in the art. The catheter body groove usually will have an inner diameter ranging from about 0.0145 inches to 0.03 inches, preferably from about 0.016 inches to 0.02 inches. The groove will typically have includes transverse ends. The groove transverse ends may overlap, abut, or have an opening formed therebetween. The opening between the transverse ends may range from about 00.1 inches to about 0.1 inches, and usually from about 0.001 inches to about 0.014 inches. The groove may generally have a length in the range from about 1 centimeters (cm) to about 200 cm, usually from about 1 cm to about 150 cm, and typically from about 10 cm to about 150 cm.

In one embodiment, the catheter body will preferably be free from structure which might interfere with the introduction of the balloon structure over the proximal end of the catheter body. Optionally, a hemomostatis structure may be provided within the proximal end of the guidewire receiving lumen. It is preferred that the hemomostatis structure does not add to the profile of or otherwise affect the catheter body such that it would interfere with loading of the balloon structure. Alternatively, a removable hub may be provided, which preferably upon its removal, the proximal end of catheter body is sufficiently free of protruding structure to permit introduction of the balloon structure thereover. When the inflation lumen is provided within the catheter body, it will be usually be necessary to provide a removable hub at the proximal end of the catheter body to permit inflation of the balloon through a port on the hub.

The devices of the present invention may be available independently or as an assembly. Optionally, the assembly may be an aggregate assembly further including at least a second treatment or diagnostic structure. When available as an assembly, usually, the first balloon structure will be preloaded over the catheter body and the assembly is sterilized and packaged as a complete unit. The second treatment or diagnostic structure, such as a second balloon structure, has a passage which is slidably receivable over the catheter body. The second balloon structure may be included as part of a single aggregate assembly together with the first balloon structure and the catheter body, or it may be available as a separate package for use with the catheter body or the assembly of the present invention. Typically, the second balloon structure will differ from the first in someway, such as the dimensions, including diameter, length, or both; shape; balloon material; balloon characteristics such as compliance, flexibility, elasticity or the like; or other features. In a particular example, at least one of the balloon structures, usually the second balloon structure may carry a stent or other vascular prosthesis. Usually, but not necessarily, the first balloon structure is intended for performing angioplasty or other therapeutic or diagnostic procedure with the second balloon structure being intended to deliver a stent after the angioplasty treatment. Other examples include drug infusion balloons, radioactive delivery balloons, atherectomy, and the like. Of course, the intravascular catheter assemblies comprising only a single balloon structure may also be adapted to carry a stent, drug infusion balloon, radioactive delivery balloon, or the like, as well.

In an embodiment, the intravascular catheter and/or assemblies of the present invention may further comprise a deployable embolic capture element on either or both the catheter body and the balloon structure. The deployable embolic capture element may comprise coils, wires, braids, mesh, and the like and take on a variety of shapes such as funnel or parachute shapes. Preferably, the embolic capture element is formed from a nickel-titanium alloy (such as Nitinol™ alloy), spring stainless steel, or like materials and may additionally be coated or contained by a polymer material. The expandable embolic capture element allows for filtering and/or suctioning of any emboli (which may potentially occlude a body lumen) before, during, and/or after treatment with the intravascular catheter. The embolic filter will generally have micro size holes in the range of about 1 micron (um) to about 200 um, usually from about 1 um to about 100 microns for the retrieval of emboli. The embolic filter may be released open and closed, at least in part, by axial or radial movement of the balloon structure or the catheter body.

In another embodiment, the intravascular catheters and/or assemblies of the present invention may further comprise a second expandable balloon on the catheter body configured to be distal to the first balloon structure. The second balloon may have dimensions, characteristics, and be formed from materials, similar to the first balloon structure described above. The second balloon itself may also carry an expandable vascular prosthesis that is balloon expandable. In some instances, the first balloon structure may perform angioplasty or other therapeutic or diagnostic procedures while the second balloon may be intended to deliver a stent (balloon expandable) after the angioplasty treatment. Thus, such an embodiment advantageously allows for sequential treatments in a single catheter structure.

In another embodiment, the intravascular catheters of the present invention may comprise a self-expanding vascular prosthesis on the catheter body. The self-expanding prosthesis may be formed from steel, nickel titanium, shape memory alloy, cobalt, composite material, and the like. Typically, the self-expanding prosthesis will be deployed, at least in part, by axial or radial movement of the first balloon structure or the catheter body.

Alternatively, a separate manipulation shaft could be attached to the balloon structure with a separate inflation structure, either attached directly to the balloon structure or optionally provided in the catheter body. In the later case, the catheter body will include an inflation lumen and the balloon structure will include an inflation port which mates with the inflation lumen in order to permit inflation of the balloon through the catheter body. A separate manipulation shaft will then be provided on the balloon structure extending proximally from the balloon structure when the balloon is disposed near the distal end of the catheter body.

In a method embodying features of the present invention a balloon structure according to the present invention and including an axial groove is advanced over a guidewire to a target site within a corporeal body. The guidewire may thereafter be advanced and/or retracted within the corporeal body while at least a portion of the guidewire is received within the catheter structure axial groove. The placement of the guidewire within the axial groove provides better push strength to the guidewire enhancing the advancement of the guidewire within the corporeal body.

In another embodiment, a method for catheter exchange over a catheter body comprises withdrawing a balloon structure coaxially over the catheter body while the catheter body remains in place over a guidewire within the corporeal body (e.g., vessel). The balloon structure is withdrawn proximally, usually so that it may be removed over a proximal end of the catheter body. After withdrawing a first balloon structure, a second balloon structure is introduced over the catheter body in distal direction while the catheter body remains in place over the guidewire. Typically, the second balloon structure will be introduced over the proximal end of the catheter body. A particular advantage of this method is that the first balloon structure and catheter body maybe introduced over a short guidewire (i.e. one that is only slightly longer than the angioplasty catheter itself e.g. 10 cm to 35 cm) in the manner of an over-the-wire angioplasty catheter with the advantage that the first balloon structure may be withdrawn from over the proximal end of the catheter body and exchanged for a subsequent (second ) balloon structure. As the balloon structures themselves will be shorter than the catheter body, typically being from 3 cm to 50 cm, they can be withdrawn without losing manual access to the proximal ends of the catheter body and short guidewire.

In an exemplary protocol using the intravascular balloon catheters and methods of the present invention, the intravascular catheter comprising a first balloon structure preloaded over a catheter body is first introduced together with a guidewire to a target region in the vasculature in a conventional manner. Usually, a distal end of the guidewire, extends beyond the distal end of the catheter body by a short distance as the intravascular catheter assembly is being advanced. In that way, a short guidewire can be used where the guidewire is fully supported in the guidewire lumen of the catheter body, which typically runs the entire length of the catheter body.

After the first balloon structure has been positioned at the target location within the vasculature, e.g. a stenosed region within the coronary vasculature, the first balloon may be expanded to treat the target region, e.g. by opening the stenosed region. Thus, the first balloon structure may act as an angioplasty balloon. The balloon, usually, being substantially non-distensable at the relatively high inflation pressure used, typically from about 3 atmospheres to about 20 atmospheres. Alternatively, the first structure may be any other type of therapeutic or diagnostic catheter including other types of balloons.

After the initial treatment is completed, the balloon structure may be withdrawn proximally from over the catheter body. This may be accomplished by using the inflation tube when the balloon structure includes such an inflation tube. Otherwise, withdrawal may typically be accomplished using a shaft, such as a solid core wire or hypotube attached to the balloon structure and extending proximally therefrom. The passage of the balloon structure, as described above, will usually be relatively short so that the balloon structure may be withdrawn from over the proximal end of the catheter body and guidewire, with the lengths of the catheter body and guidewire being extended a small amount to allow manual access while the balloon structure is being withdrawn thereover.

After the first balloon structure has been withdrawn, the second balloon structure may be introduced over the proximal ends of both the guidewire and the catheter body. Again, the length of the passage in the second balloon structure will typically be in the range from about 3 cm to 50 cm, so that manual access to both the catheter body and guidewire will remain at all times. The second balloon structure may be advanced using either an inflation tube or other manipulation shaft overextending proximally from the balloon structure. The balloon structure will then be advanced until it reaches a location near the distal end of the catheter body where it can be further positioned within the treatment region. In the exemplary case, the second balloon structure will carry a balloon expandable stent or other vascular prosthesis, where the stent is implanted by expansion of the second balloon structure.

Optionally, further treatments can be provided, e.g. using a third coaxial sleeve structure which could carry drugs, genes, radiation, or other therapeutic agents or modalities. The third coaxial structure may, but need not, also comprise an inflatable balloon. The third structure usually may be introduced in a manner analogous to the introduction of the second balloon structure, as described. As can be appreciated, more treatment steps may be performed using multiple structures by successively introducing balloon, sleeve, and other structures over the catheter body. Moreover, it is also contemplated that two or more balloon structures may be introduced over the catheter body at the same time.

After the patient treatment is completed, the intravasculature catheter structure which remains over the guidewire will be withdrawn. In a first option, the catheter and guidewire can be withdrawn simultaneously where the catheter is never in the vasculature without the guidewire present in the guidewire lumen. Alternatively, the balloon or other coaxial sleeve structure can be withdrawn from over the catheter body prior to removing the catheter body and guidewire simultaneously. As a third option, the catheter body may be provided with an axial slit or break away portion to permit removal of the catheter body from over the guidewire with the guidewire remaining in place. In that way the guidewire would remain in place for subsequent use with other catheters or devices.

BRIEF DESCRIPTION OF THE DRAWINGS

FIG. 1A is an elevational, partially cutaway, view of a balloon structure embodying features of the invention.

FIGS. 1B through 1G are transverse cross-sectional view of the balloon structure of FIG. 1A taken along their respective lines.

FIG. 1I is an elevational, partially cutaway, view of an alternate embodiment of the balloon structure of FIG. 1A further including an axially collapsible catheter body having a telescopic configuration and affixed to a passage.

FIG. 1J is an elevational, partially cutaway, view of an alternate embodiment of the balloon structure of FIG. 1A further including an axially collapsible catheter body having a convoluted configuration and affixed to a passage.

FIG. 2A is an elevational, partially cut away, view of a catheter body embodying features of the invention.

FIGS. 2B through 2C are cross-sectional view of the balloon structure of FIG. 1A taken along their respective lines.

FIG. 4A is an elevational, partially cutaway, view of the balloon structure of FIG. 1 and the catheter body of FIG. 2 together as an assembly.

FIGS. 4B through 4E are transverse cross-sectional view of the assembly of FIG. 4A taken along their respective lines.

FIG. 5A is an elevational, partially cutaway, view of an embodiment of the assembly of FIG. 4A showing the catheter body at least partially received within an axial groove of the balloon structure.

FIG. 5B is a transverse cross-sectional view of the assembly of FIG. 5A taken along line 5B-5B.

FIG. 6 is an elevational view, partially cutaway, view of an alternate embodiment of the balloon structure of FIG. 4 with the catheter body and balloon structure separate from one another.

FIGS. 7 through 9 are transverse cross-sectional views of the balloon structure of FIG. 6 taken along their respective lines.

FIGS. 10 and 11 are transverse cross-sectional views of the catheter body of FIG. 6 taken along their respective lines.

FIG. 13 is a transverse cross-sectional view taken along line 13-13 of FIG. 12.

FIGS. 13A and 13' are alternate embodiments of FIG. 13.

DETAILED DESCRIPTION OF THE INVENTION

Figure 1F:
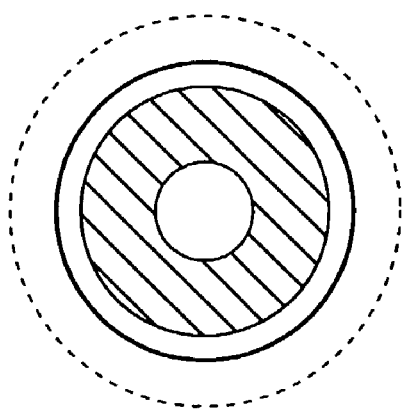
Figure 1G:
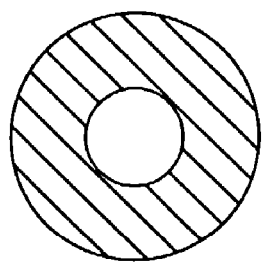

FIGS. 1A through 1G illustrate features of an intravascular catheter 10 embodying features of the present invention and generally including a balloon structure 14 having an elongate shaft 26 having a proximal end 32, a distal end 36, and proximal and distal sections 15 and 17. At least one lumen such as an inflation lumen 29 extends along at least a portion of the shaft terminating at a point proximal to the distal end of the shaft. The shaft may be of a unitary construction or formed from more than one fluidically connected portions.

An expandable member, such as an inflatable member (e.g., balloon) 40 having an interior chamber 42 is disposed at the distal section of the elongate shaft 26. The chamber, such as an inflation chamber, is in fluid communication with the inflation lumen 29. The inflation lumen usually has a length in the range from 10 cm to 150 cm.

The shaft further includes a sleeve portion 38 at the shaft distal section, having an axial passage 41 therethrough which is configured to be slidably disposed over an elongate body such as elongate body 12 shown in FIG. 2A or a guidewire. For example, the passage is configured to be receivable over the elongate body or slidably receive the elongate body. At least a portion of the sleeve forms the inflation lumen 29 extending within the inflatable member.

The sleeve may be formed as an integral part of the shaft. Alternatively, the sleeve portion, as shown in FIG. 1A, may be formed from a separate element sealingly attached to a tubular member forming a portion of the shaft extending proximal to the sleeve.

The sleeve portion may include one or more lumens. In the case of multiple lumens, one lumen is an inflation lumen 30 and another lumen forming a catheter body passage 31 for receiving the catheter body. The multiple lumens of the sleeve portion 38 may be of a unitary construction or from different tubular members having lumens extending therein.

The balloon 40 is disposed over at least a portion of the sleeve portion 38 and is sealingly secured at balloon proximal and distal ends to the sleeve. Alternatively, the balloon may be formed integral with the sleeve. Usually, the sleeve portion has a longitudinal dimension greater than that of the balloon and extends distal to the balloon distal end.

The sleeve portion may have a length in the range from about 3 cm to about 50 cm, usually from about 4 cm to about 40 cm, and typically from about 5 cm to about 25 cm. The balloon or other expandable structure will generally have a length less than that of the sleeve, usually much shorter, typically being in the range from about 1 cm to about 5 cm, often from about 2 cm to about 4 cm. The sleeve passage 41 has a diameter which is large enough to be introduced over the catheter body, usually being from 0.4 mm to 4 mm, more usually from 0.8 mm to 2 mm. The sleeve 38 is usually a single lumen tube, but in other embodiments could be a multiple lumen tube where only one of the lumens is intended to receive the catheter body 13. Other lumens could be provided for perfusion or other purposes. The sleeve may be formed from conventional catheter materials, typically being an extruded polymer tube.

Figure 1H:
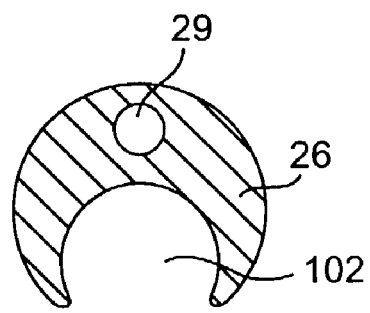
FIG. 1H is a transverse cross-sectional view of an alternate embodiment of the catheter structure of FIG. 1A including an axial groove extending along at least a portion of its length.

The balloon structure 14, as shown in FIG. 1H, includes an axial groove 102 extending along at least a portion of the shaft 26 so as to removably receive at least a portion of the elongate body such as a catheter or a guidewire, as shown in FIGS. 4 and 5.

The balloon structure groove 102 is appropriately sized to accommodate elongate bodies such as conventional guidewires and catheters, as well as catheter bodies disclosed herein. The balloon structure groove will usually have an inner diameter ranging from about 0.0145 inches to 0.03 inches, preferably from about 0.016 inches to 0.02 inches. The groove will typically have includes transverse ends, 105 and 106. The groove transverse ends may overlap, abut, or have an opening 104 formed therebetween. The opening between the transverse ends may range from about 00.1 inches to about 0.1 inches, and usually from about 0.001 inches to about 0.014 inches. The groove may generally have a length in the range from about 1 centimeters (cm) to about 200 cm, usually from about 1 cm to about 150 cm, and typically from about 10 cm to about 150 cm. The balloon structure 14, as shown in FIGS. 1A and 4A, further comprises a luer or other connector 30 attached to a proximal end 32 of the shaft 26.

In an alternate embodiment, as shown in FIGS. 1I and 1J, the intravascular catheter 10 may further include a tubular member affixed to a portion of the passage, either over or inside the passage, which is axially collapsible at least along a portion of its length extending proximal to the passage. The axially collapsible tubular member may have any suitable collapsible configuration, such as a telescopic or convoluted structure, as shown respectively in FIGS. 1I and 1J.

Now referring to FIGS. 2 through 5, an intravascular catheter assembly 10 embodying features of the invention, generally comprises the balloon structure 14 and a catheter body 13, as shown in FIGS. 2 and 3, including an elongate member 12 having proximal and distal ends, 16 and 18, and a guidewire receiving lumen 20 extending along at least a portion therebetween to a port 23 at the distal end of the elongate member 12.

The catheter body may be of unitary construction or may be formed from different members fluidically connected to one another. The guidewire receiving lumen may be an integral part of the catheter body or may be formed as a lumen within another tubular body disposed within the catheter body. A perimeter of the catheter body may have any suitable shape including circular, oblong, or elliptical shape. Optionally, a tapered cone 22, atraumatic tip, or other distal structure may be provided at the distal end 18 in order to facilitate introduction of the catheter body through the vasculature. The cone 22 may have a smooth taper or it may be flared. Alternatively, the distal end of the catheter body, preferably, may be axially tapered for improved navigation through the tortuous path of the intracorporeal body, usually for a length of at least 3 millimeters (mm), typically at least about 0.5 mm, preferably at least about 0.1 mm.

Catheter body 13 will have dimensions selected to accommodate the particular target location within the vasculature to be treated. Usually the catheter body will have a length in the range from about 10 cm to about 200 cm, usually from about 50 cm to about 200 cm, typically from about 125 cm to about 150 cm for treatment of the coronary vasculature. The outer diameter of the catheter body will also be chosen depending on the intended use, with catheter bodies typically having a diameter in the range from 1 French (F; 0.33 mm) to 10 F, typically from 2 F to 5 F. The diameter of the guidewire lumen will be selected to receive a conventional coronary or other guidewire. Such guidewires typically have diameters of about 0.006 inch (0.15 mm) or about 0.008 inch (0.20 mm) to about 0.035 inch (0.89) and the guidewire lumens will typically have diameters in the range from 0.2 mm to 2 mm, usually from or 0.4 mm to 0.6 mm, respectively.

The catheter body may be formed from polymer materials, composite materials, braided materials, or metal materials. Typically, the catheter body is formed from hypotube or as extrusions of polymeric resins. Suitable resins materials include polyamides (nylons) polyamides, polyvinylchloride, PBAX, PTFE, and the like. Catheter bodies may optionally be reinforced with braids, coils, filaments or other materials in order to enhance the pushability and/or reduce the wall thickness. The tapered distal tip 22 may be formed integrally with the remainder of the catheter body 13 or may be formed separately and attached using adhesives, heat fusion, or other techniques. In some instances, the tip 22 may be formed from a particularly soft material in order enhance a traumatic introduction of the catheter.

Figure 3A:
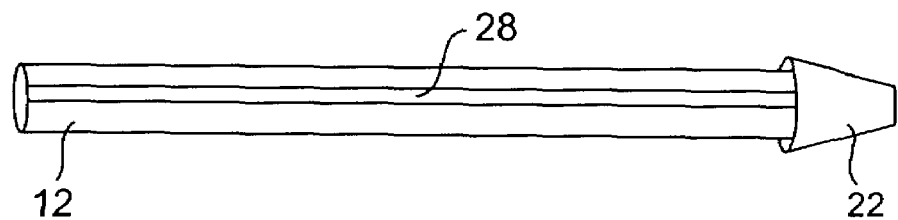
FIG. 3A is an alternate embodiment of the catheter body of FIG. 2 including axial slit.
Figure 3B:
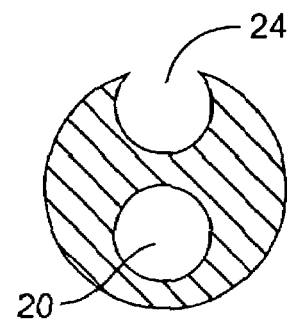
FIG. 3B is a cross-sectional view of the catheter body of FIG. 3A having an axial groove and axial slit.
Figure 3C:
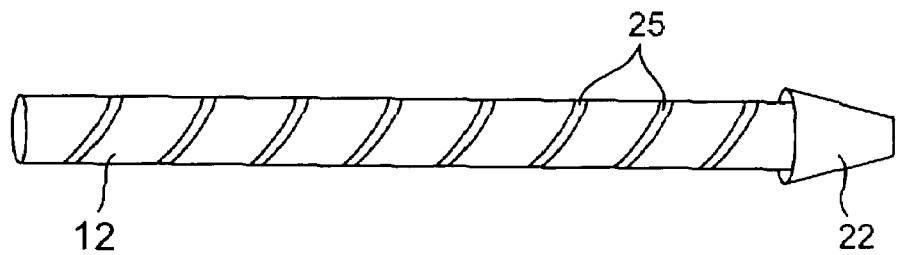
FIG. 3C is an alternate embodiment of the catheter body of FIG. 3A including a spiral slit.

In an embodiment features of which are shown in FIG. 2C, catheter body 13 may include an axial groove 24 to removably receive shaft 26 of the balloon structure 14 Inclusion of the catheter body groove 24 can reduce the overall diameter (profile) of the intravascular catheter assembly. In another embodiment features of which are shown in FIGS. 3A and 3B the catheter body includes an axial split 28 fluidically connecting the exterior surface of the catheter body to the guidewire receiving lumen to facilitate insertion or removal of the guidewire, within or from the guidewire receiving lumen. In place of slit 28, the catheter body 13 could be provided with a frangible "break way" structure to permit opening of the lumen as the catheter is withdrawn and the guidewire removed. Alternatively, the catheter body 13 may include a spiral slit 25 over at least a portion of the length of the guidewire lumen, as depicted in FIG. 3C.

The balloon 40 is initially folded over the sleeve 38, as shown in full line in both FIGS. 1A, 4A, and 5A. The balloon may be inflated by introduction of a suitable inflation medium through the inflation tube 14 to produce an inflated configuration, as shown in broken line in FIG. 1. The dimensions, materials, and other characteristics of the balloon 40 maybe as generally described in the patent and medical literature for angioplasty balloons.

Alternatively, the balloon 40 may be configured for purposes other than or in addition to angioplasty. For example, the balloon 40 may be configured to receive a stent or other balloon expandable vascular prosthesis thereover. Such vascular prostheses include both stents and graft structures, usually intended to maintain patency of a blood vessel following angioplasty. The stents which may be delivered using the balloon structures of the present inventions will usually be of the malleable or deformable type, where the stent is initially in a narrow dimension to facilitate intraluminal delivery. After placement at the target site, the stent or graft is then expanded in situ by internal inflation of the balloon 40, causing expansion of the stent or graft structure in order to maintain radial expansion after the balloon is removed. Such balloon expandable stents and grafts are well-described in the patent and medical literature. See, for example, U.S. Pat. Nos. 4,733,665; 4,776,377; 4,877,030; 5,019,090; 5,102,417; 5,123,917; 5,195,984; 5,219,355; 5,344,426; 5,360,443; 5,382,261; 5,733,303; and 5,792,018, the full disclosures of which are incorporated herein by reference.

While the present invention will usually employ a conventional inflatable balloon as part of the balloon structure, it will also be possible to incorporate other radially expansible devices which are generally recognized in the art to be equivalent to inflatable balloons for the purpose of performing angioplasty and other intravascular interventional procedures. Such "balloon equivalents" include expansible shafts, expansible cages, modified balloons (such as half balloons, balloons with channels, etc.), malecots, and the like. Examples of alternative structures are taught in U.S. Pat. Nos. 5,944,691; 5,533,968; and 6,048,484, the full disclosures of which are taught herein by reference.

It will be appreciated that, due to their modular nature, the intravascular balloon catheters 10 of the present invention may include more than one balloon structure, where the different balloon structures are often intended for different purposes. In a first particular example, the intravascular balloon catheters may include a first balloon structure intended for angioplasty and a second balloon structure 14 intended for stent placement. In the later case, the second balloon structure will usually have the stent preloaded over the balloon. Alternatively, of course it will be possible crimp the stent over the balloon immediately prior to use (i.e. in the hospital rather than at the point of manufacturing).

Referring to FIGS. 6-11, an alternative intravascular balloon catheter 50 constructed in accordance with the principles of the present inventions will be described. Intravascular balloon catheter 50, comprises a catheter body 52 and a balloon structure 54. The catheter body 52 has a proximal end 56, a distal end 58, and a guidewire lumen 60 (FIGS. 10 and 11) therethrough. In contrast to catheter body 13 of intravascular balloon catheter assembly 10 the catheter body 52 of the second embodiment also includes a balloon inflation lumen 62 extending the entire length from proximal end 56 to distal end 58 thereof. To introduce both the guidewire through the guidewire lumen 60 and an inflation medium through the inflation lumen 62, a proximal hub 64 is removably attached to the proximal end 56 of the catheter body 52. The hub includes both an inflation port 66 and a guidewire port 68, typically in the form of a hemostasis valve. The proximal hub 64 will be removable in order to permit introduction of the balloon structure 54 there-over. Specific designs for removable catheter hubs which are able to connect to inflation lumens are provided in U.S. Pat. No. 5,810,869, the full disclosure of which is incorporated herein by reference. A tapered distal nosecone 70 may optionally be mounted at the distal end 58 of the catheter body 52. The nosecone 70 may be similar nosecone 22 described in the earlier embodiment.

The balloon structure 54 comprises a balloon assembly 72 including an sleeve 74 having a balloon 76 disposed there-over. Inflation of the balloon 76 is provided through inflation lumen 62 in the catheter body 52. Inflation lumen 62 terminates in a port 78 (FIG. 11) formed on a proximal surface of the nosecone 70. A connector 80 on the balloon assembly 72 mates with the port 78 when the balloon is properly positioned at the distal end of the catheter body 52. An inflation medium introduced through the lumen 62 will reach the balloon in order to inflate the balloon.

The balloon structure 54 further includes a shaft 82 which is attached to a proximal end of the sleeve 74 and which extends proximally there-from. Since the shaft is not needed for inflation, it can have a solid core as shown in FIG. 7. The shaft 82, however, will be sufficiently long and will have sufficient column strength in order to introduce a passage 84 of the balloon structure 54 over the catheter body 52. The proximal hub 64 can be removed whenever the lumen assembly 72 of the balloon structure 54 is to be introduced over or withdrawn over the proximal end 56 of the catheter body 52. At all other times, the proximal hub 54 may be placed over the proximal end of the catheter body in order to provide hemostasis for the guidewire as well as permit connection of the inflation source (not shown) to the balloon 76.

Figure 12:
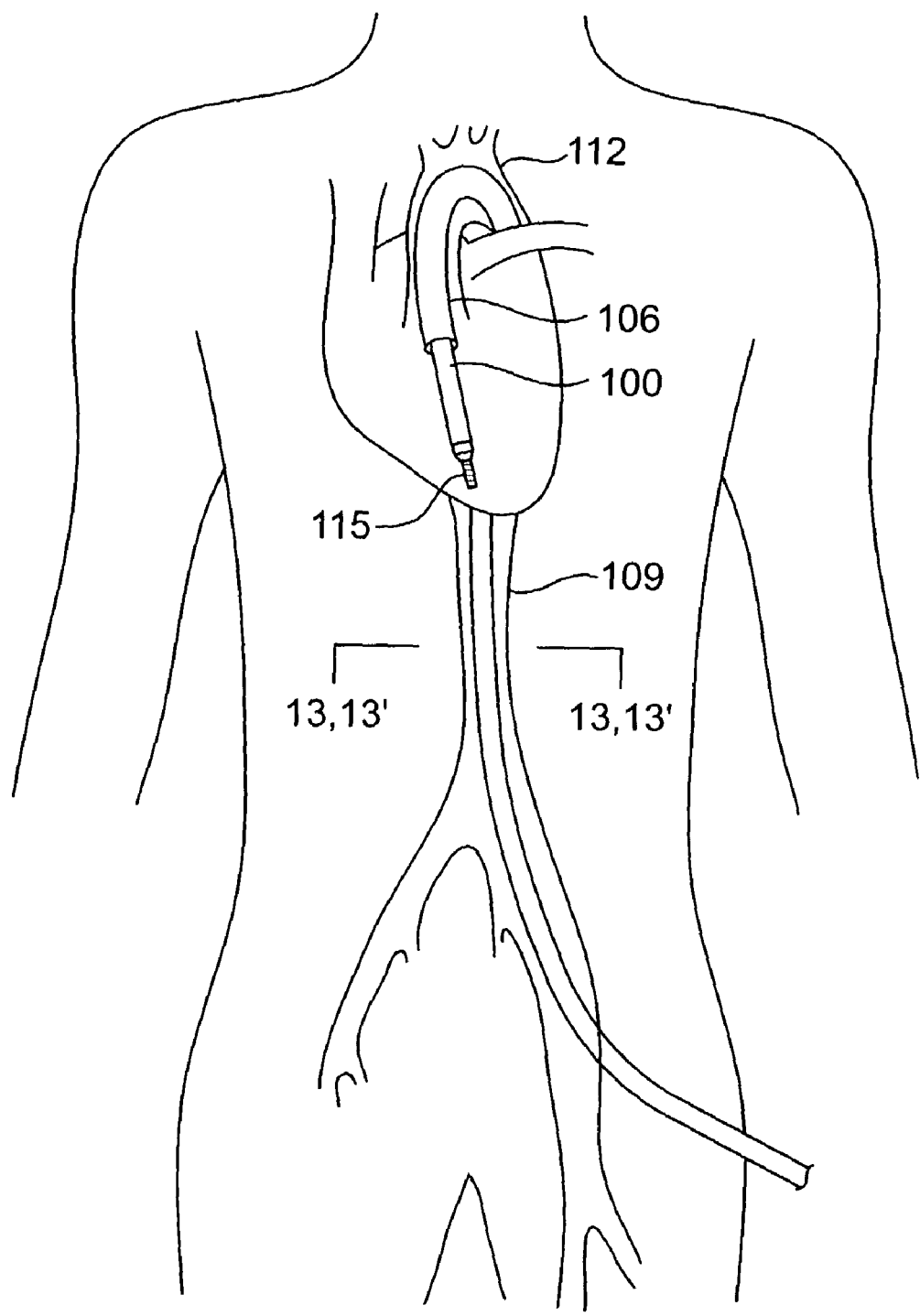
FIG. 12 is a schematic of an embodiment of an introduction of the balloon catheter of FIG. 4 to a region in the coronary vasculature.

Referring now to FIGS. 12,13, and 14A-14H, use of the intravascular balloon catheter 10 for performing balloon angioplasty followed by stent treatment of a coronary artery and a patient P will be described. A balloon catheter 10 may be introduced to a target site in the coronary vasculature through a guide catheter GC and over a guidewire GW, as illustrated in FIGS. 12 and 13. The intravasculature balloon catheter 10 is introduced in through the guiding catheter GC via hemostatic valve and sheath (not shown) and through the femoral artery A (or any blood vessel) to the coronary vasculature over the aortic arch AA.

Alternatively, as shown in FIG. 13A, the tubular-catheter body 13 may comprise an axial slit 24 for removably receiving the inflation tube 14, and the guidewire lumen 20 may be axially slit 28 to permit removal and/or introduction of the guidewire.

Figure 14A:
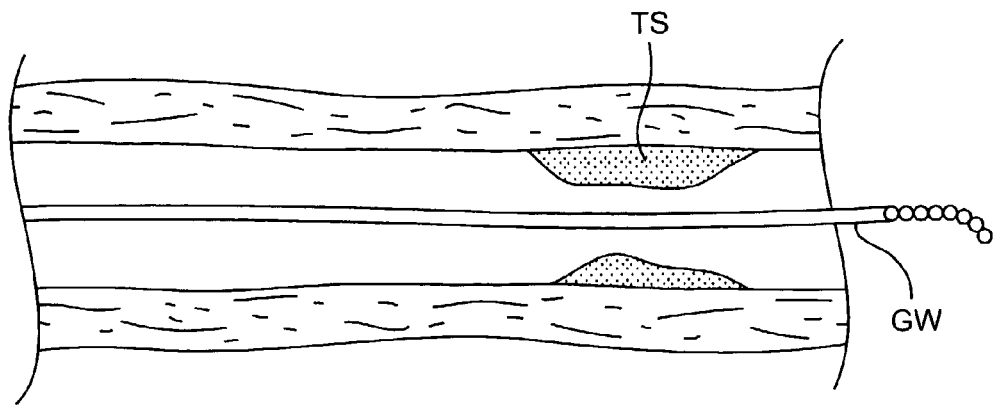
FIGS. 14A-14H are elevational, partially cutaway, views of an embodiment of the steps in an exemplary method preformed according to the present invention.
Figure 14B:
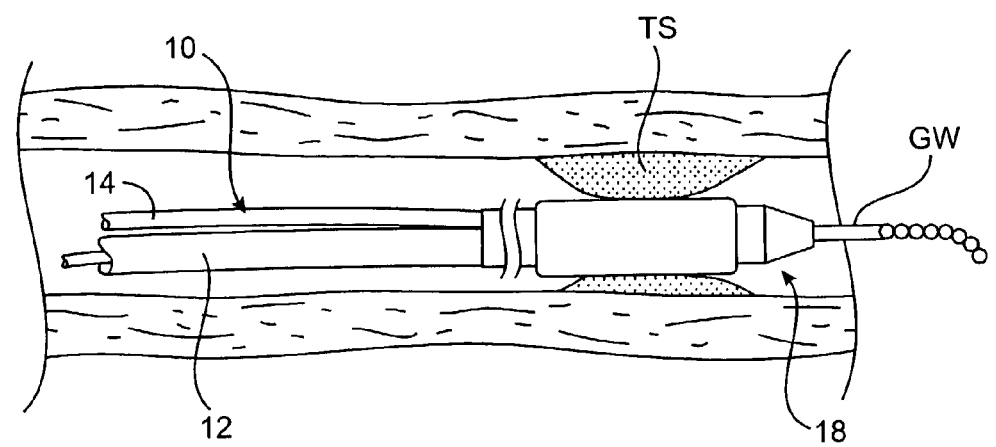

As shown in FIG. 14A, the guidewire GW will usually be positioned at the target site TS, typically a region of stenosis to be treated by balloon angioplasty. Usually, the balloon catheter 10 and guidewire GW will be introduced together with the guidewire being periodically extended forward of the distal end 18 of the catheter until the target site is reached, as shown in FIG. 14B.

Figure 14C:
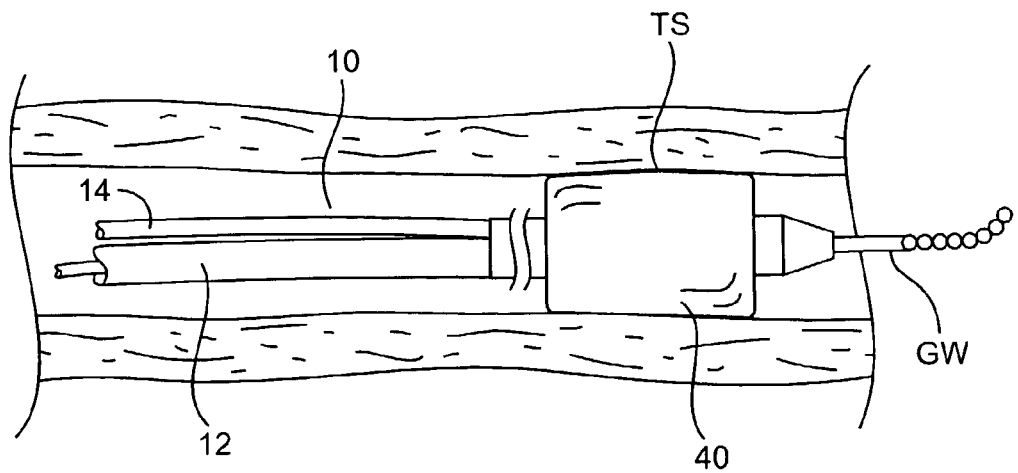
Figure 14D:
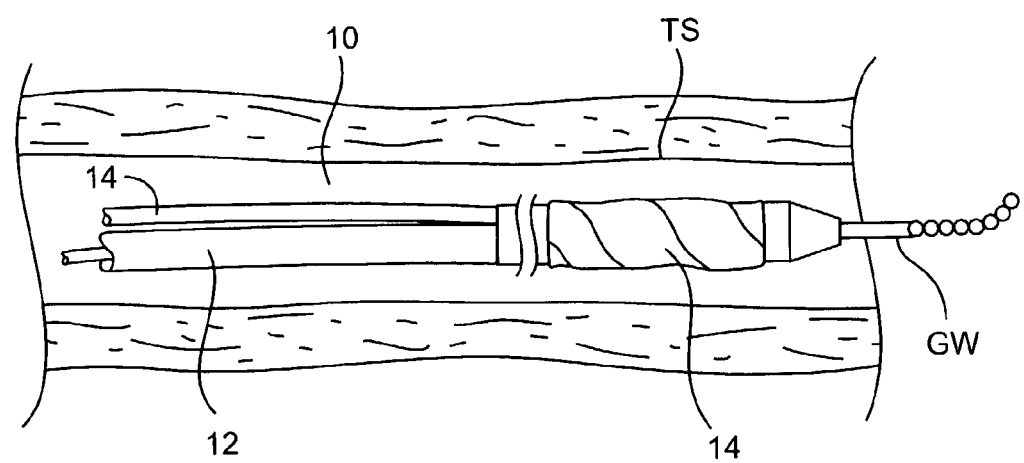
Figure 14E:
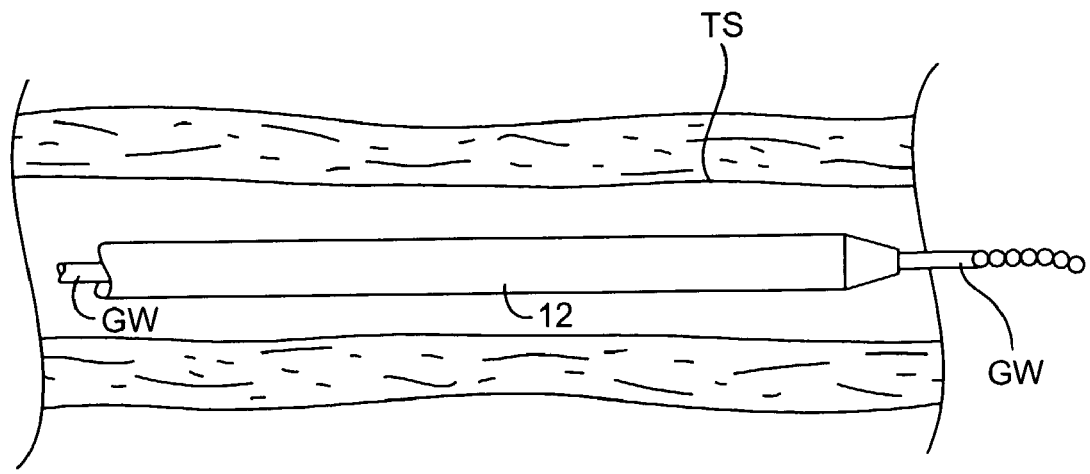
Figure 14F:
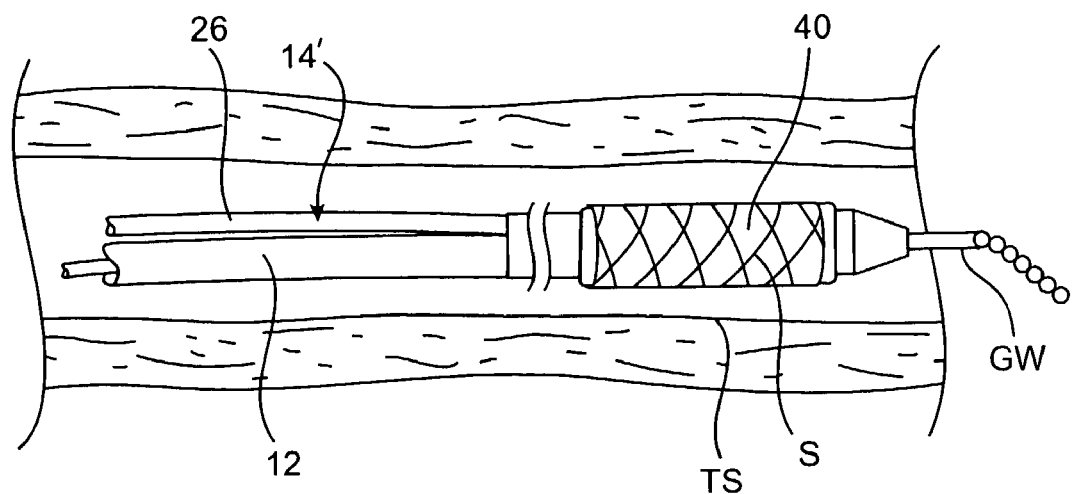
Figure 14G:
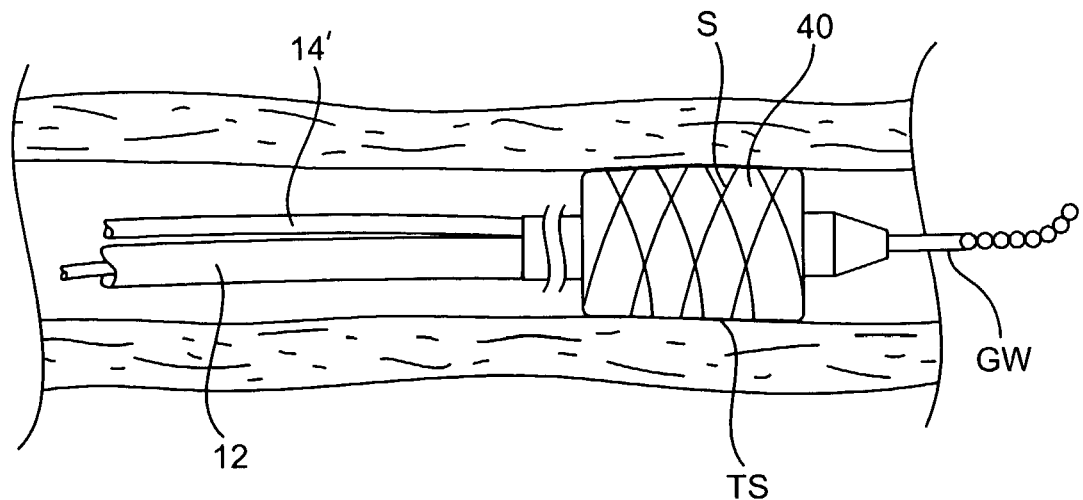

Once at the target site, TS the balloon 40 is inflated as shown in FIG. 14C, in order to expand the occlusion at the target site TS. After the balloon angioplasty treatment is completed, the balloon 40 will be deflated, as shown in FIG. 14D, with guidewire GW and/or the catheter body remaining in place. The balloon structure 14 may then be removed from over the catheter body 13, as shown in FIG. 14E, again with the guidewire GW remaining in place. A second balloon structure 14' may then be introduced over the catheter body 13 by pushing the balloon assembly 34 distally using shaft 26 (FIG. 14F). After the balloon assembly 34 is in place, a stent S which is in place over the balloon assembly may be deployed by inflating balloon 40, as shown in FIG. 14G. Preferably, the guidewire GW remains in place, while the balloon structures 14 and 14' have been exchanged over the catheter body 13.

Figure 14H:
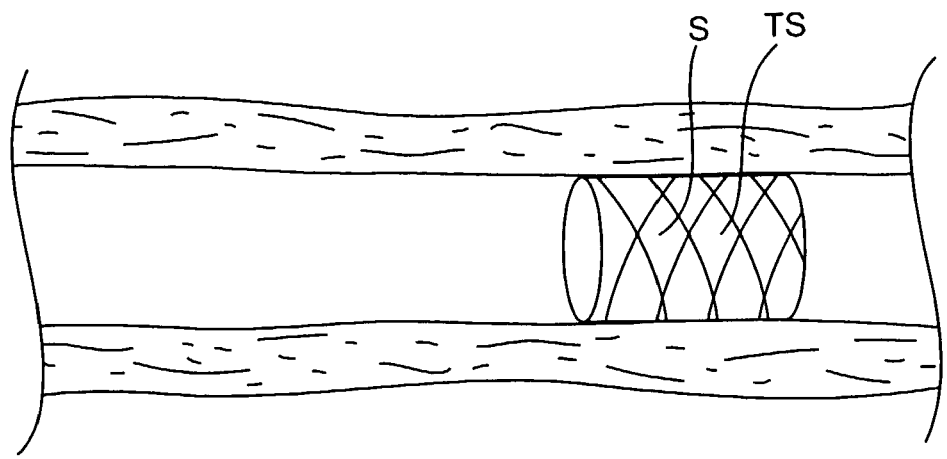

After the stent S has been properly deployed, balloon 40 may be deflated and the catheter 10 removed. Removal of catheter 10 may be effected simultaneously with removal of the guidewire, i.e. the catheter, including both the catheter body 13 and balloon structure 14', may be withdrawn simultaneously with the guidewire. Alternatively, the balloon structure 14' could be removed first, with the guidewire GW and the catheter body 13 then being withdrawn simultaneously. As still a further alternative, the guidewire GW may be left in place by withdrawing the catheter body 13 over guidewire GW. When the guidewire GW is a short guidewire, it will be advantageous to provide means in the catheter body for pulling the guidewire from the guidewire lumen as the catheter body is withdrawn. For example, the catheter body could include an axial split in order to permit withdrawal of the guidewire as the tubular catheter bodies withdrawn. This allows the treating physician to maintain a hold on the guidewire as the catheter body is withdrawn. Alternatively, catheter body could have a splitable structure which permits the catheter body to be peeled part as the catheters withdrawn. Peeling apart catheter also permits the treating physician to have access to the guidewire at all times of the withdrawal of the catheter body 13. Again, the procedure, the stent S will remain in place within the target site, as illustrated in FIG. 14H.

Figure 15:
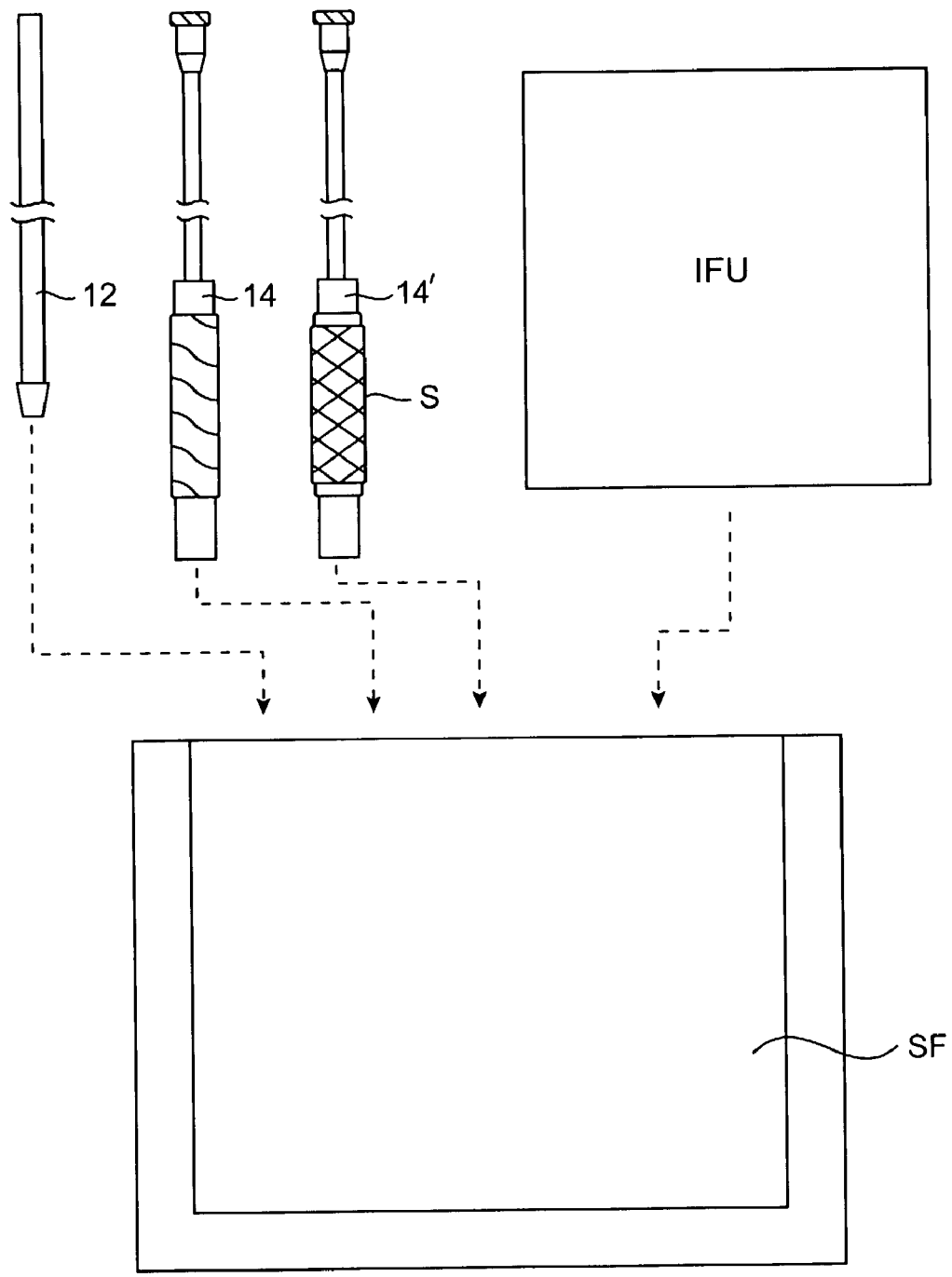
FIG. 15 is an elevational view of a kit embodying features of the invention.

The system components of the balloon catheters of the present invention may be configured as kits as shown in FIG. 15. The kits may comprise any one or more of the system components together with instructions for use IFU and/or sterile packaging SP. Usually, the kits will comprise at least a catheter body, e.g. catheter body 13, and one balloon structure, e.g. balloon structure 14. Optionally, the kit will include at least a second balloon structure 14, and the second structure may carry a balloon expansible or other vascular prosthesis, e.g. an stent S. The IFU may set forth any of the methods described herein.

Figure 16A:
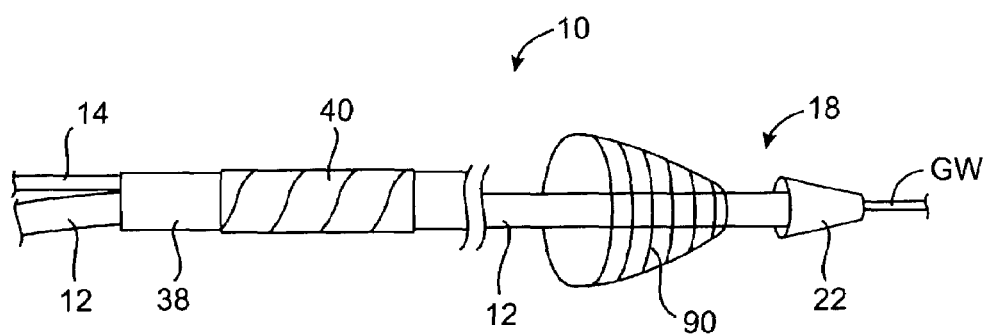
FIG. 16A is an elevational, partially cutaway, view of an alternate embodiment of the balloon catheter assembly of FIG. 4 with a deployable embolic capture element on the catheter body.
Figure 16B:
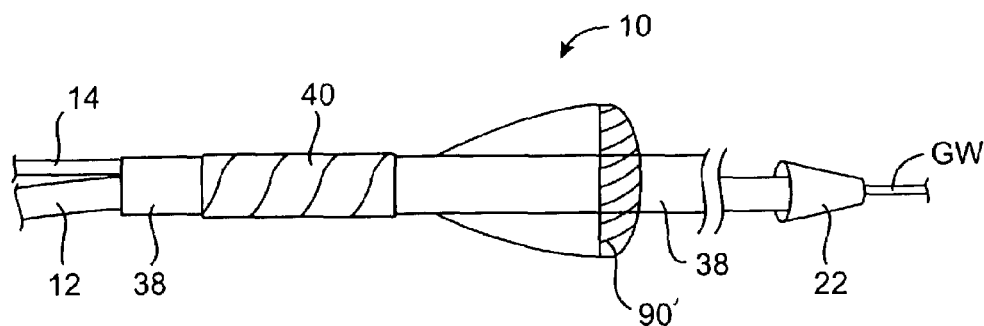
FIG. 16B is an elevational, partially cutaway, view of an alternate embodiment of the balloon catheter assembly of FIG. 4 with a deployable embolic capture element on the first balloon structure.

Referring now to FIG. 16A, an intravascular balloon catheter 10 may further comprise a deployable embolic capture element 90 on the catheter body 13, typically located within 20 cm of the distal end 18 of the catheter body 13. Alternatively, the intravascular balloon catheter 10 may comprise a deployable embolic capture element 90' on the sleeve 38 of the first balloon structure 14, as depicted in FIG. 16B. The deployable embolic capture element 90, 90' may comprise coils, wires, braids, mesh, and the like and take on a variety of shapes, i.e., a funnel shape (FIG. 16A), a parachute shape (FIG. 16B), etc. Preferably, the embolic capture element 90, 90' is formed from a nickel-titanium alloy (such as Nitinol™ alloy), spring stainless steel, or like materials and may additionally be contained or coated with a polymer material. The expandable embolic capture element 90, 90' allows for filtering and/or suctioning of any emboli (which may potentially occlude a body lumen) before, during, and/or after treatment with the intravascular balloon catheter 10. The embolic filter 90, 90' will typically have micro size holes in the range of about 1 micron to 100 microns for the retrieval of emboli, wherein the embolic filter is released open and closed, at least in party, by axial or radial movement of the inflatable balloon structure 40 or the catheter body 13.

Figure 17A:
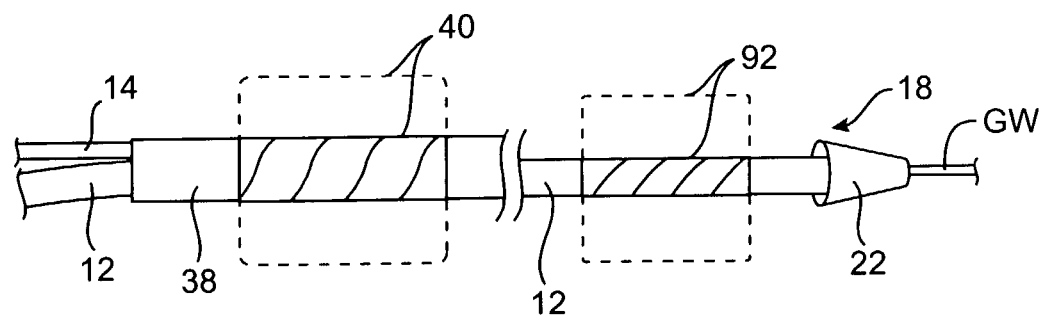
FIG. 17A is an elevational, partially cutaway, view of an alternate embodiment of the balloon catheter assembly of FIG. 4 with a second balloon on the catheter body.
Figure 17B:
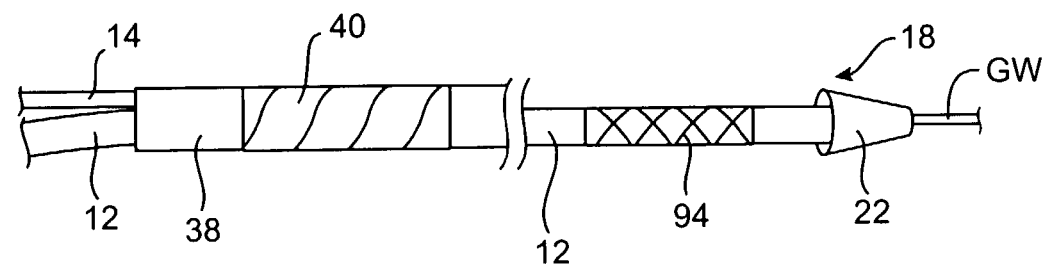
FIG. 17B is an elevational, partially cutaway, view of an alternate embodiment of the balloon catheter assembly of FIG. 4 with an expandable vascular prosthesis.

Referring now to FIGS. 17A and 17B, the intravascular balloon catheters 10 of the present invention may further comprise a second expandable balloon 92 on the catheter body 13, under, proximal, or distal the first balloon structure 40. The second balloon 92 will have dimensions, characteristics, and be formed from materials similar to the first balloon structure 40, as described above. The second balloon 92 itself may also carry a balloon expandable vascular prosthesis 94, as illustrated in FIG. 17B. In some instances, the first balloon structure 40 may perform angioplasty or other therapeutic or diagnostic procedures, while the second balloon 92 may be intended to deliver a stent 94 after the angioplasty treatment. Thus, such an embodiment advantageously allows for sequential treatments in a single catheter structure. Alternatively, the intravascular balloon catheter of the present invention may comprise a self-expanding vascular prosthesis on the catheter body, typically located within 20 cm of the distal end of the catheter body. The vascular prosthesis may be positioned distal to the first balloon structure or at least partially or fully under the first balloon structure in the unexpanded state. The self-expanding prosthesis may be formed from steel, nickel titanium, shape memory alloy, cobalt, composite material, and the like. Typically, the self-expanding prosthesis will be deployed, at least in part, by axial or radial movement of the first balloon structure or the catheter body.

Figure 18:
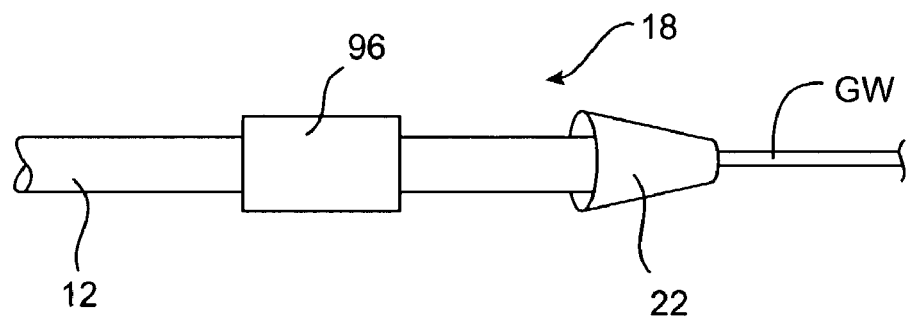
FIG. 18 is an elevational, partially cutaway, view of an alternate embodiment of the balloon catheter assembly of FIG. 4 with an atherectomy element.
Figure 19:
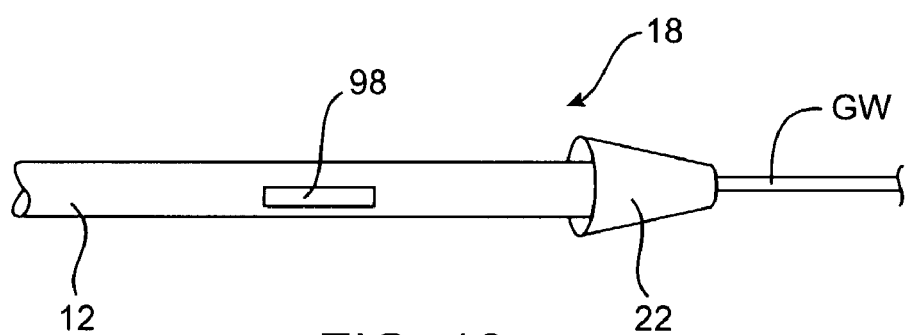
FIG. 19 is an elevational, partially cutaway, view of an alternate embodiment of the balloon catheter assembly of FIG. 4 with a pressure sensor.
Figure 20:
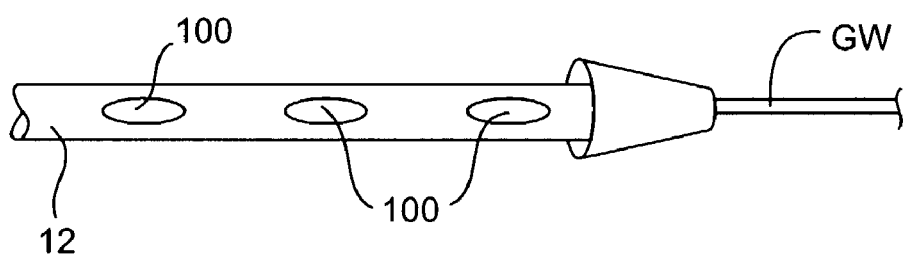
FIG. 20 is an elevational, partially cutaway, view of an alternate embodiment of the balloon catheter assembly of FIG. 4 with an infusion port.

Referring now to FIG. 18, the intravascular balloon catheters 10 of the present invention may further comprise an atherectomy element 96 coupled to the distal end 18 of the catheter body 13. Those skilled in the art will recognize that the atherectomy element may comprise a blade element, a malecot, coils, wires, braids, mesh, and any other structure suitable for occlusion removal in a body lumen. FIG. 19 illustrates that the intravascular balloon catheters 10 of the present invention may further comprise a pressure sensor 98 coupled to the distal end 18 of the catheter body 13. The pressure sensor 98 may comprise a piezoelectric crystal, a resistive device, or the like and will typically monitor a pressure across a stenosed blood vessel. FIG. 20 illustrates that the intravascular balloon catheters 10 of the present invention may further comprise at least one infusion port 100 at the distal end 18 of the catheter body 13. The infusion ports 100 will typically be in fluid communication with an infusion/guidewire lumen (not shown) in the catheter body. The infusion ports allow for therapeutic drugs to be directly infused into a treatment site.

Although certain preferred embodiments and methods have been disclosed herein, it will be apparent from the foregoing disclosure to those skilled in the art that variations and modifications of such embodiments and methods may be made without departing from the true spirit and scope of the invention. Therefore, the above description should not be taken as limiting the scope of the invention which is defined by the appended claims.

What is claimed is:

1. An intravascular balloon catheter comprising:
  a catheter body having a proximal end a distal end, and a guidewire lumen therebetween; and
  a first balloon structure having a shaft with a balloon inflation lumen, a balloon sleeve fixed at a distal end of the shaft and having an inflatable balloon thereon, and a sleeve passage therethrough which is slidably receivable over the catheter body, wherein said shaft has an axial groove present along at least a portion thereof to removably receive at least a portion of the catheter body, and wherein said shaft extends proximally of the balloon sleeve and has sufficient column strength to advance the balloon structure over the catheter body.

2. An intravascular balloon catheter comprising:
  a catheter body having a proximal end, a distal end, and a guidewire lumen therebetween; and
  a first balloon structure including a shaft and a balloon sleeve fixed at a distal end of the shaft, said balloon sleeve having an inflatable balloon thereon and a sleeve passage for slidably receiving the catheter body, and said shaft having an axial groove present along at least a portion thereof for receiving at least a portion of the catheter body, wherein the shaft has sufficient column strength to advance the balloon structure over the catheter body.

3. An intravascular balloon catheter as in claim 1 or 2, wherein the catheter body comprises a tubular member having at least one lumen in addition to the guidewire lumen.

4. An intravascular balloon catheter as in claim 1 or 2, wherein a perimeter of the catheter body has a circular, oblong, or elliptical shape.

5. An intravascular balloon catheter as in claim 1 or 2, wherein the distal end of the catheter body is axially tapered for a length of at least 3 mm.

6. An intravascular balloon catheter as in claim 1 or 2, wherein the distal end of the catheter body is axially tapered for a length of at least 0.5 mm.

7. An intravascular balloon catheter as in claim 1 or 2, wherein the distal end of the catheter body is axially tapered for a length of at least 0.1 mm.

8. An intravascular balloon catheter as in claim 1 or 2, further comprising an atraumatic tip at the distal end of the catheter body.

9. An intravascular balloon catheter as in claim 1 or 2, wherein the balloon structure distal end is distally tapered.

10. An intravascular balloon catheter as in claim 1 or 2, wherein the catheter body is formed at least in part from a polymer material, a composite material, a braided material, a metal material, or a metal alloy.

11. An intravascular balloon catheter as in claim 1 or 2, wherein the catheter body is formed from a metal alloy comprising a nickel titanium alloy.

12. An intravascular balloon catheter as in claim 1 or 2, wherein the catheter body comprises multiple tubular members coupled to one another.

13. An intravascular balloon catheter as in claim 1 or 2, wherein the groove has a length in the range from 10 cm to 150 cm and an opening in the range from 0.001 inches to 0.014 inches.

14. An intravascular balloon catheter as in claim 1 or 2, wherein the inflation lumen has a length in the range from 10 cm to 150 cm.

15. An intravascular balloon catheter as in claim 1 or 2, wherein the catheter body is substantially free from structure at the proximal end which would interfere with passage of the balloon structure over the proximal end of the catheter body.

16. An intravascular balloon catheter as in claim 1 or 2, wherein the catheter body has a length in the range from 50 cm to 200 cm, and outer diameter in the range from 1 F to 10 F, and a guidewire lumen diameter in the range from 0.2 mm to 2 mm.

17. An intravascular balloon catheter as in claim 1 or 2, wherein the balloon structure further comprises the inflatable balloon disposed over an outer surface of the sleeve, wherein the passage is formed axially in the sleeve.

18. An intravascular balloon catheter as in claim 17, wherein the sleeve has a length in the range form 3 cm to 50 cm and the inflatable balloon has a length in the range from 1 cm to 5 cm.

19. An intravascular balloon catheter as in claim 1 or 2, wherein the balloon structure further comprises the inflatable balloon disposed over at least a portion of the sleeve, wherein the passage is an axial passage distal to a balloon chamber.

20. An intravascular balloon catheter as in claim 1 or 2, wherein the guidewire lumen extends from the catheter body proximal end to a distal tip at the catheter body distal end.

21. An intravascular balloon catheter as in claim 1 or 2, wherein the catheter body comprises multiple tubular members fluidically connectable to one another.

22. An intravascular balloon catheter as in claim 1 or 2, wherein the groove is a single continuous groove.

23. An intravascular balloon catheter as in claim 1 or 2, wherein the groove includes multiple intermittent grooves.

24. An intravascular balloon catheter as in claim 1 or 2, wherein the groove includes transverse ends.

25. An intravascular balloon catheter as in claim 24, wherein the groove has an opening formed between the transverse ends in the range from 0.001 inches to 0.1 inches.

26. An intravascular balloon catheter as in claim 25, wherein the groove has an opening formed between the transverse ends in the range from 0.001 inches to 0.014 inches.

27. An intravascular balloon catheter as in claim 1 or 2, wherein the groove has a length in the range from about 1 cm to about 200 cm.

28. An intravascular balloon catheter as in claim 27, wherein the groove has a length in the range from about 1 cm to about 150 cm.

29. An intravascular balloon catheter as in claim 28, wherein the groove has a length in the range from about 10 cm to about 150 cm.

30. An intravascular balloon catheter as in claim 1 or 2, wherein the groove has an inner diameter in the range of about 0.0145 to 0.03 inches.

31. An intravascular balloon catheter as in claim 30, wherein the groove has an inner diameter in the range of about 0.016 to 0.02 inches.

32. An intravascular balloon catheter as in claim 1, or 2, wherein the catheter body distal end includes a distal tip configured to be slidably disposable distal to a distal tip of the balloon structure.

33. An intravascular balloon catheter as in claim 1 or 2, wherein the balloon structure includes a distal portion lumen with multiple lumens.

34. An intravascular balloon catheter as in claim 1 or 2, wherein the balloon structure comprises multiple lumens in a distal portion of the structure.

35. An intravascular balloon catheter as in claim 1 or 2 wherein the sleeve forming the passage includes multiple lumens along at least a portion thereof.

* * * * *